(12) United States Patent
Backus et al.

(10) Patent No.: US 11,065,113 B2
(45) Date of Patent: Jul. 20, 2021

(54) PROSTHETIC HEART VALVE HAVING AN IMPROVED TUBULAR SEAL

(71) Applicant: BOSTON SCIENTIFIC SCIMED, INC., Maple Grove, MN (US)

(72) Inventors: Andrew J. H. Backus, Santa Cruz, CA (US); Loren M. Crow, Santa Cruz, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 137 days.

(21) Appl. No.: 16/139,256

(22) Filed: Sep. 24, 2018

(65) Prior Publication Data
US 2019/0021853 A1 Jan. 24, 2019

Related U.S. Application Data

(63) Continuation of application No. 15/059,840, filed on Mar. 3, 2016, now Pat. No. 10,080,652.

(60) Provisional application No. 62/133,048, filed on Mar. 13, 2015.

(51) Int. Cl.
*A61F 2/24* (2006.01)

(52) U.S. Cl.
CPC .......... *A61F 2/2418* (2013.01); *A61F 2/2439* (2013.01); *A61F 2210/0057* (2013.01); *A61F 2220/0075* (2013.01); *A61F 2250/0003* (2013.01); *A61F 2250/006* (2013.01); *A61F 2250/0037* (2013.01); *A61F 2250/0069* (2013.01)

(58) Field of Classification Search
CPC ....................................................... A61F 2/82
USPC .................................................. 623/1.1–2.38
See application file for complete search history.

(56) References Cited

U.S. PATENT DOCUMENTS

| | | |
|---|---|---|
| 1,080,652 A | 12/1913 | Peters |
| 2,682,057 A | 6/1954 | Lord |
| 2,701,559 A | 2/1955 | Cooper |
| 2,832,078 A | 4/1958 | Williams |
| 3,099,016 A | 7/1963 | Lowell |
| 3,113,586 A | 12/1963 | Edmark, Jr. |
| 3,130,418 A | 4/1964 | Head et al. |
| 3,143,742 A | 8/1964 | Cromie |
| 3,334,629 A | 8/1967 | Cohn |
| 3,367,364 A | 2/1968 | Cruz, Jr. et al. |
| 3,409,013 A | 11/1968 | Henry |
| 3,445,916 A | 5/1969 | Schulte |

(Continued)

FOREIGN PATENT DOCUMENTS

| | | |
|---|---|---|
| CN | 1338951 A | 3/2002 |
| DE | 19532846 A1 | 3/1997 |

(Continued)

OTHER PUBLICATIONS

US 8,062,356 B2, 11/2011, Salahieh et al. (withdrawn)

(Continued)

*Primary Examiner* — Yashita Sharma
(74) *Attorney, Agent, or Firm* — Seager, Tufte & Wickhem LLP

(57) ABSTRACT

A tubular seal includes an outflow end region and an inflow end region. The inflow end region is a portion of a polymeric web retaining a woven fabric, wherein the woven fabric has a non-linear edge defining an interface between the inflow end region and the outflow end region.

9 Claims, 22 Drawing Sheets

(56) References Cited

U.S. PATENT DOCUMENTS

| | | |
|---|---|---|
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Goodenough et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King |
| 3,997,923 A | 12/1976 | Possis |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Helmut |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,388,735 A | 6/1983 | Ionescu et al. |
| 4,406,022 A | 9/1983 | Roy |
| 4,423,809 A | 1/1984 | Mazzocco |
| 4,425,908 A | 1/1984 | Morris |
| 4,470,157 A | 9/1984 | Love |
| 4,484,579 A | 11/1984 | Meno et al. |
| 4,501,030 A | 2/1985 | Ernest |
| 4,531,943 A | 7/1985 | Van Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Toshinobu et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 7,258,696 B2 | 8/2007 | Rabkin et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | L et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,674,282 B2 | 3/2010 | Wu et al. |
| 7,712,606 B2 | 5/2010 | Salahieh et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,846,204 B2 | 12/2010 | Letac et al. |
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,328,868 B2 | 7/2012 | Paul et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |

(56) References Cited

U.S. PATENT DOCUMENTS

| | | |
|---|---|---|
| 8,308,798 B2 | 11/2012 | Pintor et al. |
| 8,323,335 B2 | 12/2012 | Rowe et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,778,020 B2 | 7/2014 | Gregg et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0029014 A1 | 5/2002 | Jayaraman |
| 2002/0052651 A1 | 5/2002 | Myers et al. |
| 2002/0055767 A1 | 5/2002 | Forde et al. |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171803 A1 | 9/2003 | Shimon |
| 2003/0176884 A1 | 9/2003 | Berrada et al. |
| 2003/0176912 A1 | 9/2003 | Chuter et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0195620 A1 | 10/2003 | Huynh et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0006344 A1 | 1/2004 | Nguyen et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |

(56) References Cited

U.S. PATENT DOCUMENTS

| | | |
|---|---|---|
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | Wasdyke |
| 2005/0113910 A1 | 5/2005 | Paniagua et al. |
| 2005/0124937 A1 | 6/2005 | Kick et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjlemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0135981 A1 | 6/2006 | Lenker et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrman et al. |
| 2007/0021768 A1 | 1/2007 | Nance et al. |
| 2007/0055340 A1 | 3/2007 | Pryor |
| 2007/0061008 A1 | 3/2007 | Salahieh et al. |
| 2007/0112355 A1 | 3/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0171456 A1 | 7/2009 | Kveen et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2010/0023120 A1 | 1/2010 | Holecek et al. |
| 2010/0049313 A1 | 2/2010 | Alon et al. |
| 2010/0094392 A1 | 4/2010 | Nguyen et al. |
| 2010/0094399 A1 | 4/2010 | Dorn et al. |
| 2010/0100176 A1* | 4/2010 | Elizondo ............ A61F 2/2418 623/2.38 |
| 2010/0121434 A1 | 5/2010 | Paul et al. |

(56) References Cited

U.S. PATENT DOCUMENTS

| | | |
|---|---|---|
| 2010/0191326 A1 | 7/2010 | Alkhatib |
| 2010/0219092 A1 | 9/2010 | Salahieh et al. |
| 2010/0280495 A1 | 11/2010 | Paul et al. |
| 2011/0257735 A1 | 10/2011 | Salahieh et al. |
| 2011/0276129 A1 | 11/2011 | Salahieh et al. |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0197379 A1 | 8/2012 | Laske et al. |
| 2012/0277850 A1 | 11/2012 | Bertini |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030520 A1 | 1/2013 | Lee et al. |
| 2013/0090729 A1* | 4/2013 | Gregg .................. A61F 2/2415 623/2.38 |
| 2013/0116778 A1 | 5/2013 | Gregg et al. |
| 2013/0123796 A1 | 5/2013 | Sutton et al. |
| 2013/0158656 A1 | 6/2013 | Sutton et al. |
| 2013/0190865 A1 | 7/2013 | Anderson |
| 2013/0304199 A1 | 11/2013 | Sutton et al. |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243967 A1 | 8/2014 | Salahieh et al. |
| 2014/0350668 A1 | 11/2014 | Delaloye et al. |
| 2015/0327995 A1 | 11/2015 | Morin et al. |
| 2016/0067042 A1* | 3/2016 | Murad .................. A61F 2/2427 623/2.17 |

FOREIGN PATENT DOCUMENTS

| | | |
|---|---|---|
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9829057 A1 | 7/1998 |
| WO | 9836790 A1 | 8/1998 |
| WO | 9850103 A1 | 11/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 03003949 A2 | 1/2003 |
| WO | 03011195 A2 | 2/2003 |
| WO | 03028592 A1 | 4/2003 |
| WO | 03030776 A2 | 4/2003 |
| WO | 03037227 A2 | 5/2003 |
| WO | 03047648 A2 | 6/2003 |
| WO | 03015851 B1 | 11/2003 |
| WO | 03094793 A1 | 11/2003 |
| WO | 03094797 A1 | 11/2003 |
| WO | 2004006803 A1 | 1/2004 |
| WO | 2004006804 A1 | 1/2004 |
| WO | 2004014256 A1 | 2/2004 |
| WO | 2004019811 A2 | 3/2004 |
| WO | 2004019817 A1 | 3/2004 |
| WO | 2004021922 A2 | 3/2004 |
| WO | 2004023980 A2 | 3/2004 |
| WO | 2004026117 A2 | 4/2004 |
| WO | 2004037333 A1 | 5/2004 |
| WO | 2004041126 A1 | 5/2004 |
| WO | 2004043293 A2 | 5/2004 |
| WO | 2004047681 A1 | 6/2004 |
| WO | 2004058106 A2 | 7/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005062980 A2 | 7/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2006138391 A2 | 12/2006 |
| WO | 2007033093 A2 | 3/2007 |
| WO | 2007035471 A2 | 3/2007 |
| WO | 2007044285 A2 | 4/2007 |
| WO | 2007053243 A2 | 5/2007 |
| WO | 2007058847 A2 | 5/2007 |
| WO | 2007092354 A2 | 8/2007 |
| WO | 2007097983 A2 | 8/2007 |
| WO | 2010017537 A2 | 2/2010 |
| WO | 2010042950 A2 | 4/2010 |
| WO | 2012116368 A2 | 8/2012 |
| WO | 2013033791 A1 | 3/2013 |
| WO | 2014140230 A1 | 9/2014 |
| WO | 20140145811 A1 | 9/2014 |
| WO | 2015085218 A1 | 6/2015 |

OTHER PUBLICATIONS

US 8,062,357 B2, 11/2011, Salahieh et al. (withdrawn)
US 8,075,614 B2, 12/2011, Salahieh et al. (withdrawn)
US 8,211,170 B2, 07/2012, Paul et al. (withdrawn)
US 8,133,271, 11/2011, Salahieh et al. (withdrawn)
Topol, "Percutaneous Expandable Prosthetic Valves." Textbook of Interventional Cardiology, W.B. Saunders Company, 2: 1268-1276, 1994.
International Search Report and Written Opinion PCT/US2016/014401, dated Jul. 12, 2016.
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Bodnar et al., "Replacement Cardiac Valves R Chapter 13: Extinct Cardiac Valve Prostheses." Pergamon Publishing Corporation. New York, 307-322, 1991.
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study."

(56) References Cited

OTHER PUBLICATIONS

Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Hijazi "Transcatheter Valve Replacement: A New Era of Percutaneous Cardiac Intervention Begins." J. of Am. College of Cardio., 43(6): 1088-1089, Mar. 17, 2004.
Huber et al., "Do Valved Stents Compromise Coronary Flow?" European Journal of Cardio-thoracic Surgery, vol. 25: 754-759, Jan. 23, 2004.
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Moulopoulos et al., "Catheter-Mounted Aortic Valves." Annals of Thoracic Surg., 11(5): 423-430, May 1971.
Paniagua et al., "Percutaneous Heart Valve in the Chronic in Vitro Testing Model." Circulation, 106: e51-e52, Sep. 17, 2002.
Paniagua et al., "Heart Watch." Texas Heart Institute. Edition: 8 pages, Spring, 2004.
Pavcnik et al., "Percutaneous Bioprosthetic Venous Valve: A Longterm Study in Sheep." J. of Vascular Surg., 35(3): 598-603, Mar. 2002.
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Sochman et al., "Percutaneous Transcatheter Aortic Disc Valve Prosthesis Implantation: A Feasibility Study." Cardiovasc. Intervent. Radiol., 23: 384-388, Sep. 2000.
Stuart, "In Heart Valves, A Brave, New Non-Surgical World." Start-Up. Feb. 9-17, 2004.
Stassano, "Mid-term Results of the Valve-on-Valve Technique for Bioprosthetic Failure." European Journal of Cardiothoracic Surgery: vol. 18, 453-457, Oct. 2000.
"A Matter of Size." Triennial Review of the National Nanotechnology Initiative, The National Academies Press, Washington DC, v-13, http://www.nap.edu/catalog/11752/a-matter-of-size-triennialreview-of-the-national-nanotechnology, 2006.
Cunanan et al., "Tissue Characterization and Calcification Potential of Commercial Bioprosthetic Heart Valves." Ann. Thorac. Surg., S417-421, May 15, 2001.
Laborde et al., "Percutaneous Implantation of the Corevalve Aortic Valve Prosthesis for Patients Presenting High Risk for Surgical Valve Replacement." Eurointervention: 472-474, Feb. 2006.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
Zhou et al, "Self-expandable Valved Stent of Large Size: Off-Bypass Implantation in Pulmonary Position." Eur. J. Cardiothorac, 24: 212-216, Aug. 2003.
US 8,062,356, 11/2011, Salahieh et al. (withdrawn)
US 8,062,357, 11/2011, Salahieh et al. (withdrawn)
US 8,075,614, 12/2011, Salahieh et al. (withdrawn)
US 8,133,271, 3/2012, Salahieh et al. (withdrawn)
US 8,211,170, 7/2012, Paul et al. (withdrawn)
Andersen et al., "Transluminal implantation of artificial heart valves. Description of a new expandable aortic valve and initial results with implantation by catheter technique in closed chest pigs." Euro. Heart J., 13:704-708, 1992.
Atwood et al., "Insertation of Heart Valves by Catheterization." Project Supervised by Prof. S. Muftu of Northeastern University 2001-2002: 36-40.
Bodnar et al., "Replacement Cardiac Valves R Chapter 13: Extinct Cardiac Valve Prostheses." Pergamon Publishing Corporation. New York, 1991: 307-322.
Boudjemline et al., "Percutaneous Implantation of a Biological Valve in the Aorta to Treat Aortic Valve Insufficiency—A Sheep Study." Med Sci. Monit., vol. 8, No. 4: BR113-116, 2002.
Boudjemline et al., "Percutaneous Implantation of a Valve in the Descending Aorta in Lambs." Euro. Heart J., 23: 1045-1049, 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, 2004.
Boudjemline et al., "Percutaneous Valve Insertion: A New Approach?" J. of Thoracic and Cardio. Surg, 125(3): 741-743, 2003.
Boudjemline et al., "Steps Toward Percutaneous Aortic Valve Replacement." Circulation, 105: 775-778, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, 2004.
Cribier et al., "Percutaneous Transcatheter Implementation of an Aortic Valve Prosthesis for Calcific Aortic Stenosis: First Human Case Description." Circulation, 106: 3006-3008, 2002.
Cribier et al., "Percutaneous Transcatheter Implantation of an Aortic Valve Prosthesis for Calcific Aortic Stenosis: First Human Case." Percutaneous Valve Technologies, Inc., 16 pages, 2002. Ferrari et al., "Percutaneous Transvascular Aortic Valve Replacement with Self-Expanding Stent-Valve Device." Poster from the presentation given at SMIT 2000, 12th International Conference. Sep. 5, 2000.
Hijazi, "Transcatheter Valve Replacement: A New Era of Percutaneous Cardiac Intervention Begins." J. of Am. College of Cardio., 43(6): 1088-1089, 2004.
Huber et al., "Do Valved Stents Compromise Coronary Flow?" European Journal of Cardio-thoracic Surgery, vol. 25: 754-759,2004.
Knudsen et al., "Catheter-implanted prosthetic heart valves." Int'l J. of Art. Organs, 16(5): 253-262, 1993.
Kort et al., "Minimally Invasive Aortic Valve Replacement: Echocardiographic and Clinical Results." Am. Heart J., 142(3): 476-481, 2001.
Love et al., The Autogenous Tissue Heart Valve: Current Status. Journal of Cardiac Surgery, 6(4): 499-507, 1991.
Lutter et al., "Percutaneous Aortic Valve Replacement: An Experimental Study. I. Studies on Implantation." J. of Thoracic and Cardio. Surg., 123(4): 768-776, 2002.
Moulopoulos et al., "Catheter-Mounted Aortic Valves." Annals of Thoracic Surg., 11(5): 423-430, 1971.
Paniagua et al., "Percutaneous Heart Valve in the Chronic in Vitro Testing Model." Circulation, 106: e51-e52, 2002.
Pavcnik et al., "Percutaneous Bioprosthetic Veno Valve: A Longterm Study in Sheep." J. of Vascular Surg., 35(3): 598-603, 2002.
Phillips et al., "A Temporary Catheter-Tip Aortic Valve: Hemodynamic Effects on Experimental Acute Aortic Insufficiency." Annals of Thoracic Surg., 21(2): 134-136, 1976.
Sochman et al., "Percutaneous Transcatheter Aortic Disc Valve Prosthesis Implantation: A Feasibility Study." Cardiovasc. Intervent. Radiol., 23: 384-388, 2000.
Stuart, "In Heart Valves, A Brave, New Non-Surgical World." Start-Up. Sep. 17, 2004.
Vahanian et al., "Percutaneous Approaches to Valvular Disease." Circulation, 109: 1572-1579, 2004.

(56) References Cited

OTHER PUBLICATIONS

Van Herwerden et al., "Percutaneous Valve Implantation: Back to the Future?" Euro. Heart J., 23(18): 1415-1416, 2002.
Zhou et al, "Self-expandable Valved Stent of Large Size: Off-Bypass Implantation in Pulmonary Position." Eur. J. Cardiothorac, 24: 212-216, 2003.
Examiner's First Report on AU Patent Application No. 2011202667, dated May 17, 2012.
"A Matter of Size." Treiennial Review of the National Nanotechnology Initiative, The National Academies Press, Washington DC, v-13, http://www.nap.edu/catalog/11752/a-matter-of-sizetriennial-review-of-the-national-nanotechnology, 2006.
Atwood et al., "Insertion of Heart Valves by Catheterization." The Capstone Design Course Report. MIME 1501-1502. Technical Design Report. Northeastern University, pp. 1-93, Nov. 5, 2007.
Aug. 19, 2011, Supplemental Search Report from EP Patent Office, EP Application No. 04813777.2.
Aug. 19, 2011, Supplemental Search Report from EP Patent Office, EP Application No. 04815634.3.
Cunanan et al., "Tissue Characterization and Calcification Potential of Commerical Bioprosthetic Heart Valves." Ann. Thorac. Surg., S417-421, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
EP Search Report dated Aug. 10, 2011 for EP Application No. 06824992.9.
"Heart Valve Materials—Bovine (cow)." Equine & Porcine Pericardium, Maverick Biosciences Pty. Lt, http://maverickbio.com/biologicalmedical-device-materials.php?htm. 2009.
Helmus, "Mechanical and Bioprosthetic Heart Valves in Biomaterials for Artificial Organs." Woodhead Publishing Limited: 114-162,2011.
Hourihan et al., "Transcatheter Umbrella Closure of Valvular and Paravalvular Leaks." JACC, Boston, Massachusetts, 20(6): 1371-1377, Nov. 15, 1992.
Laborde et al., "Percutaneous Implantation of the Corevalve Aortic Valve Prosthesis for Patients Presenting High Risk for Surgical Valve Replacement." Eurointervention: 472-474, 2006.
Levy, "*Mycobacterium chelonei* Infection of Porcine Heart Valves." The New England Journal of Medicine, Washington DC, 297(12), Sep. 22, 1977.
Supplemental Search Report from EP Patent Office, EP Application No. 05758878.2, dated Oct. 24, 2011.
"Pericardial Heart Valves." Edwards Lifesciences, Cardiovascular Surgery FAQ, Nov. 14, 2010, http://www.edwards.com/products/cardiovascularsurgeryfaq.htm.
Southern Lights Biomaterials Homepage, Jan. 7, 2011, http://www.slv.co.nz/.
Stassano, "Mid-term Results of the Valve-on-Valve Technique for Bioprosthetic Failure." European Journal of Cardiothoracic Surgery:453-457, 2000.

* cited by examiner

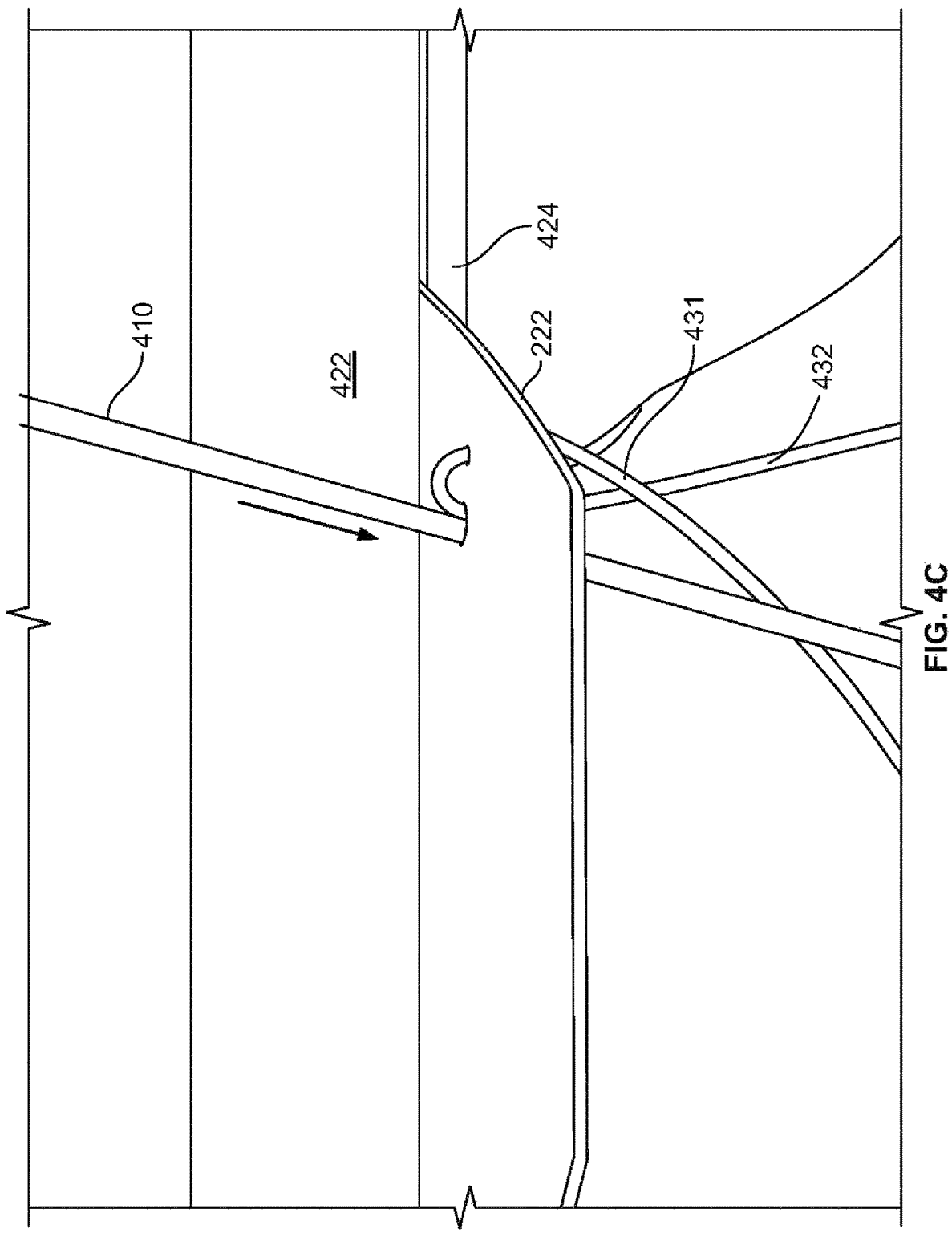

PROSTHETIC HEART VALVE HAVING AN IMPROVED TUBULAR SEAL

RELATED APPLICATIONS

This application is a continuation of U.S. application Ser. No. 15/059,840, filed Mar. 3, 2016, which claims priority to U.S. Provisional Application No. 62/133,048, filed Mar. 13, 2015.

FIELD

This document provides prosthetic heart valves having an improved tubular seal.

BACKGROUND

The human heart contains four valves: a tricuspid valve, a pulmonic valve, a mitral valve and an aortic valve. The main purpose of the valves is to maintain unimpeded forward flow of blood through the heart and the major blood vessels connected to the heart, for example, the pulmonary artery and the aorta. As a result of a number of disease processes, both acquired and congenital, any one of the four heart valves may malfunction and result in either stenosis (impeded forward flow) and/or backward flow (regurgitation). Either process burdens the heart and may lead to serious problems, for example, heart failure. Various procedures for fixing or replacing defective heart valves are known in the art. In some cases, artificial heart valves can be implanted in the heart of a patient to replace a diseased or damaged heart valve with a prosthetic equivalent to minimize stenosis and regurgitation.

Prosthetic heart valves can have a variety of designs. Two major types of prosthetic heart valves include mechanical heart valves and bioprosthetic heart valves. Mechanical heart valves can be made of synthetic materials, such as plastics or metals, while bioprosthetic heart valves can be made of biologic tissue mounted on a fabric covered plastic or metal frame. Bioprosthetic heart valves can include animal tissue, such as porcine or bovine tissue, that has been chemically treated to make the valve suitable for implantation in a human. Bioprosthetic valves do not generally require a patient to undergo anticoagulant therapy, which is typically required when using mechanical valves. But bioprosthetic valves can be more prone to device wear such as tears in the valve tissue that may require the valve to be replaced. There is therefore a need to further improve the design of bioprosthetic valves to retain its functionality during the life of the patient.

SUMMARY

Prosthetic heart valves provided herein can have a structure adapted to retain functionality during the life of the patient and to minimize stenosis and regurgitation by having an improved connection between different parts of the prosthetic heart valve.

In Example 1, a tubular seal includes an outflow end region and an inflow end region. The inflow end region can include a portion of a polymeric web retaining a woven fabric, wherein the woven fabric has a non-linear edge defining an interface between the inflow end region and the outflow end region.

In Example 2, the tubular seal of Example 1, wherein polymeric web includes an elastomeric polymer matrix and the woven fabric is retained within the elastomeric polymer matrix.

In Example 3, the tubular seal of Example 1 or Example 2, wherein the woven fabric includes non-elastic fibers.

In Example 4, the tubular seal of Example 1-3, wherein the woven fabric includes fibers in a warp direction and fibers in a waft direction, wherein the fibers in both the warp direction and the waft direction are angled with respect to a central axis of the tubular seal.

In Example 5, the tubular seal of Example 4, wherein the fibers in both the warp direction and the waft direction are angled at an angle of between 5 degrees and 70 degrees with respect to the central axis of the tubular seal.

In Example 6, the tubular seal of Example 4, wherein the fibers are arranged within the tubular member to form an angle of about 45 degrees with respect to the central axis of the tubular seal.

In Example 7, the tubular seal of one of Examples 1-6, wherein the interface of the woven fabric has a scalloped shape.

In Example 8, the tubular seal of Example 7, wherein the interface has a major radius Ra that ranges from about 0.050 inches to about 0.100 inches.

In Example 9, the tubular seal of Example 7, wherein the interface has a minor radius Ri that ranges from about from about 0.020 inches to about 0.040 inches.

In Example 10, the tubular seal of Example 7, wherein the interface has a transition zone length that ranges from about 0.110 inches to about 0.160 inches.

In Example 11, a tubular seal for a prosthetic heart valve includes an elastomeric polymer matrix and a woven fabric includes a plurality of non-elastic fibers retained within an inflow end region of the elastomeric polymer matrix. The woven fabric can include a non-linear edge within the elastomeric polymer matrix.

In Example 12, the tubular seal of one of Example 11, wherein the non-linear edge of the woven fabric has a sinusoidal or scalloped shape.

In Example 13, the tubular seal of one of Examples 11 or 12, wherein the non-elastic fibers include a polyester.

In Example 14, the tubular seal of one of Examples 11-13, wherein the elastomeric polymer matrix includes a polymer selected from polycarbonates, polyurethane, silicones, and combinations thereof.

In Example 15, the tubular seal of one of Examples 11-14, wherein the inflow end region includes a first substantially uniform thickness and an outflow end region includes median thickness that is less than the first substantially uniform thickness.

In Example 16, a prosthetic heart valve includes an expandable tubular member, a plurality of leaflets and a tubular seal. The plurality of leaflets can be secured together alongside edges and retained within the expandable tubular member, each leaflet having a bottom edge at a blood inflow end of the expandable tubular member and a free edge at a blood outflow end of the expandable tubular member. The tubular seal can include a polymeric web secured to the bottom edge of each leaflet and along an outer portion of the expandable tubular member. The tubular seal can include an outflow end region and an inflow end region. The inflow end region can be a portion of polymeric web retaining a woven fabric, wherein the woven fabric has a non-linear edge defining the interface between the inflow end region and the outflow end region.

In Example 17, the prosthetic heart valve of Example 16, wherein polymeric web includes an elastomeric polymer matrix and the woven fabric is retained within the elastomeric polymer matrix.

In Example 18, the prosthetic heart valve of Example 16, wherein the woven fabric includes the non-elastic fibers.

In Example 19, the prosthetic heart valve of Example 18, wherein the woven fabric includes fibers in a warp direction and fibers in a waft direction, wherein the fibers in both the warp direction and the waft direction are angled with respect to a central axis of the tubular seal.

In Example 20, the prosthetic heart valve of Example 19, wherein the fibers in both the warp direction and the waft direction are angled at an angle of between 5 degrees and 70 degrees with respect to the central axis of the tubular seal.

In Example 21, the prosthetic heart valve of Example 19, wherein the fibers are arranged within the tubular member to form an angle of about 45 degrees with respect to the central axis of the tubular seal.

In Example 22, the prosthetic heart valve of Example 16, wherein the woven fabric includes non-elastic fibers arranged in the polymeric web to allow the tubular seal to stretch in axial and radial directions.

In Example 23, the prosthetic heart valve of Example 16, wherein the non-linear edge of the woven fabric has a sinusoidal or scalloped shape.

In Example 24, the prosthetic heart valve of Example 16, wherein the inflow end region includes a first substantially uniform thickness and the outflow end region includes median thickness that is less than the first substantially uniform thickness.

In Example 25, the prosthetic heart valve of Example 16, wherein the outflow end region includes a plurality of grommets.

In Example 26, a tubular seal for a prosthetic heart valve includes an elastomeric polymer matrix and a woven fabric that includes a plurality of non-elastic fibers retained within an inflow end region of the elastomeric polymer matrix. The woven fabric includes a non-linear edge within the elastomeric polymer matrix.

In Example 27, the tubular seal of Example 26, wherein the non-linear edge of the woven fabric has a sinusoidal or scalloped shape defining an interface between the inflow end region and the outflow end region.

In Example 28, the tubular seal of Example 27, wherein the interface has a major radius $R_a$ that ranges from about 0.050 inches to about 0.100 inches.

In Example 29, the tubular seal of Example 27, wherein interface has a minor radius $R_i$ that ranges from about from about 0.020 inches to about 0.040 inches.

In Example 30, the tubular seal of Example 27, wherein the interface has a transition zone length that ranges from about 0.110 inches to about 0.160 inches.

In Example 31, the tubular seal of Example 26, wherein the non-elastic fibers include a polyester.

In Example 32, the tubular seal of Example 26, wherein the elastomeric polymer matrix includes a polymer selected from polycarbonates, polyurethane, silicones, and combinations thereof.

In Example 33, the tubular seal of Example 26, wherein the inflow end region includes a first substantially uniform thickness and the outflow end region includes median thickness that is less than the first substantially uniform thickness.

In Example 34, the tubular seal of Example 26, wherein a thickness for the inflow end region ranges from about 0.0016 inches to about 0.0023 inches, or from about 40 microns to about 60 microns.

In Example 35, a method includes forming at least a portion of a tubular seal that includes a woven fabric within a matrix by dipping a mandrel with a first coating composition that includes at least one elastomeric polymer. The method can also include drying the first coating composition and positioning the woven fabric on the mandrel such that fibers within the fabric are oriented at an angle of about 45 degrees with respect to a central axis of the tubular seal. The method can further include applying a second coating composition on the mandrel, the second coating composition being different than the first coating composition and removing the tubular seal from the mandrel.

Prosthetic heart valves provided herein can additionally have a reduced unexpanded profile. In some cases, prosthetic heart valves provided herein include a plurality of anchor elements. In some cases, anchor elements can be secured to an expandable tubular member. In some cases, the expandable tubular member can be a braided stent. In some cases, prosthetic heart valves provided herein include three or more leaflets. In some cases, the leaflets can have a body portion and sleeve portions one or both sides. In some cases, sides of the body portions can be secured together and sleeve portions secured to anchor elements (e.g., anchor elements attached to a braided stent). In some cases, prosthetic heart valves provided herein can include a tubular seal. In some cases, the tubular seal can be secured to bottom edges of body portions of the leaflets. In some cases, the seal can be secured to a blood inlet side of an expandable member.

Although tubular seals provided herein can be applied to a variety of prosthetic heart valves provided herein (and within the scope of the claims), additional details about the overall structure of an exemplary prosthetic heart valve are provided below.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A and 1B are perspective views of the heart valve provided herein connected to the deployment device. FIG. 1C is a side view of the exemplary prosthetic heart valve. FIGS. 1D-1I illustrate how the exemplary heart valve provided herein can be delivered by the deployment device.

FIG. 2A illustrates a rounded notch in a leaflet where a leaflet can be secured to an adjacent leaflet. FIGS. 2B and 2C illustrate a side portion of the exemplary leaflet. FIG. 2B depicts the rounded notch in an armpit of the exemplary leaflet. FIG. 2C depicts attachment elements in the armpit of the exemplary leaflet.

FIG. 3 depicts apertures in a body of the exemplary leaflet.

FIGS. 4A-4G illustrate how adjacent leaflets can be stitched together in prosthetic heart valves provided herein.

FIG. 5A shows a front view of a seal having apertures and stitch patterns used for securing the seal to the braided stent. FIG. 5B depicts a close up view of a cross stitch and a portion of a circumferential stitch used for securing the seal to the braided stent. FIG. 5C depicts a cross-sectional view showing the cross stitch and a portion of the circumferential stitch.

Like reference symbols in the various drawings indicate like elements.

DETAILED DESCRIPTION

Figure 1A:
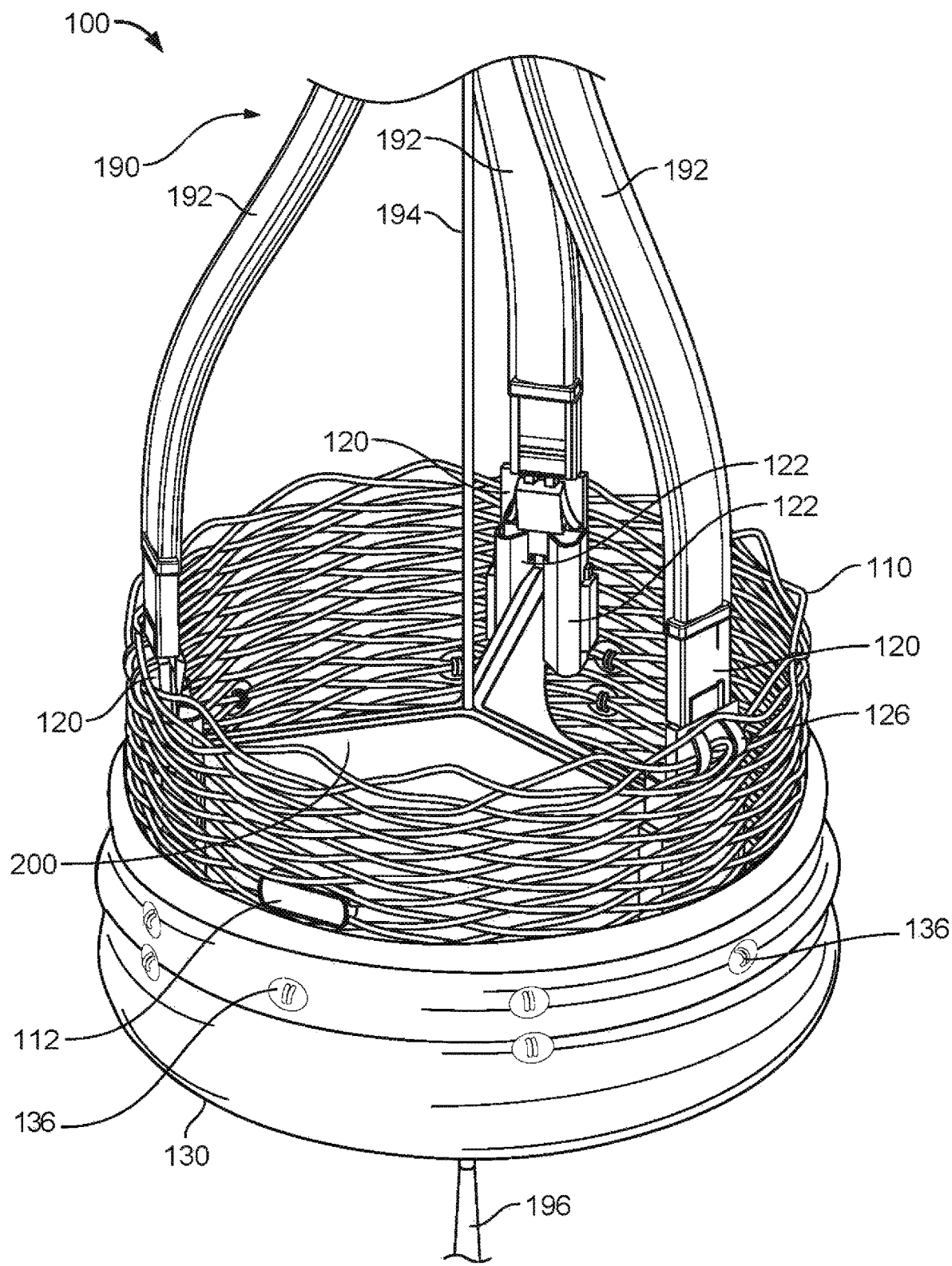
FIGS. 1A-1I illustrate an exemplary prosthetic heart valve and an exemplary deployment device provided herein.
Figure 1B:
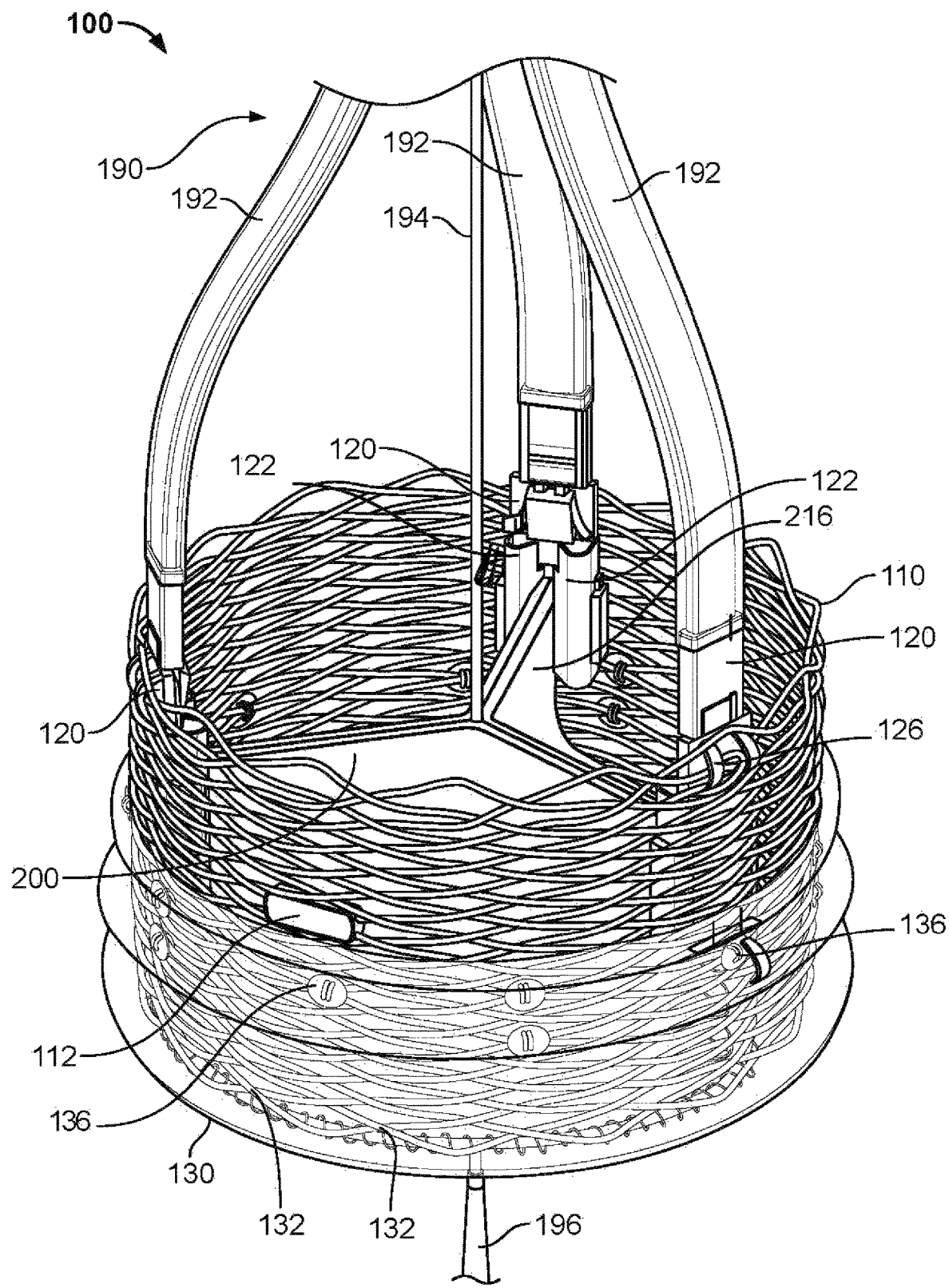
Figure 1C:
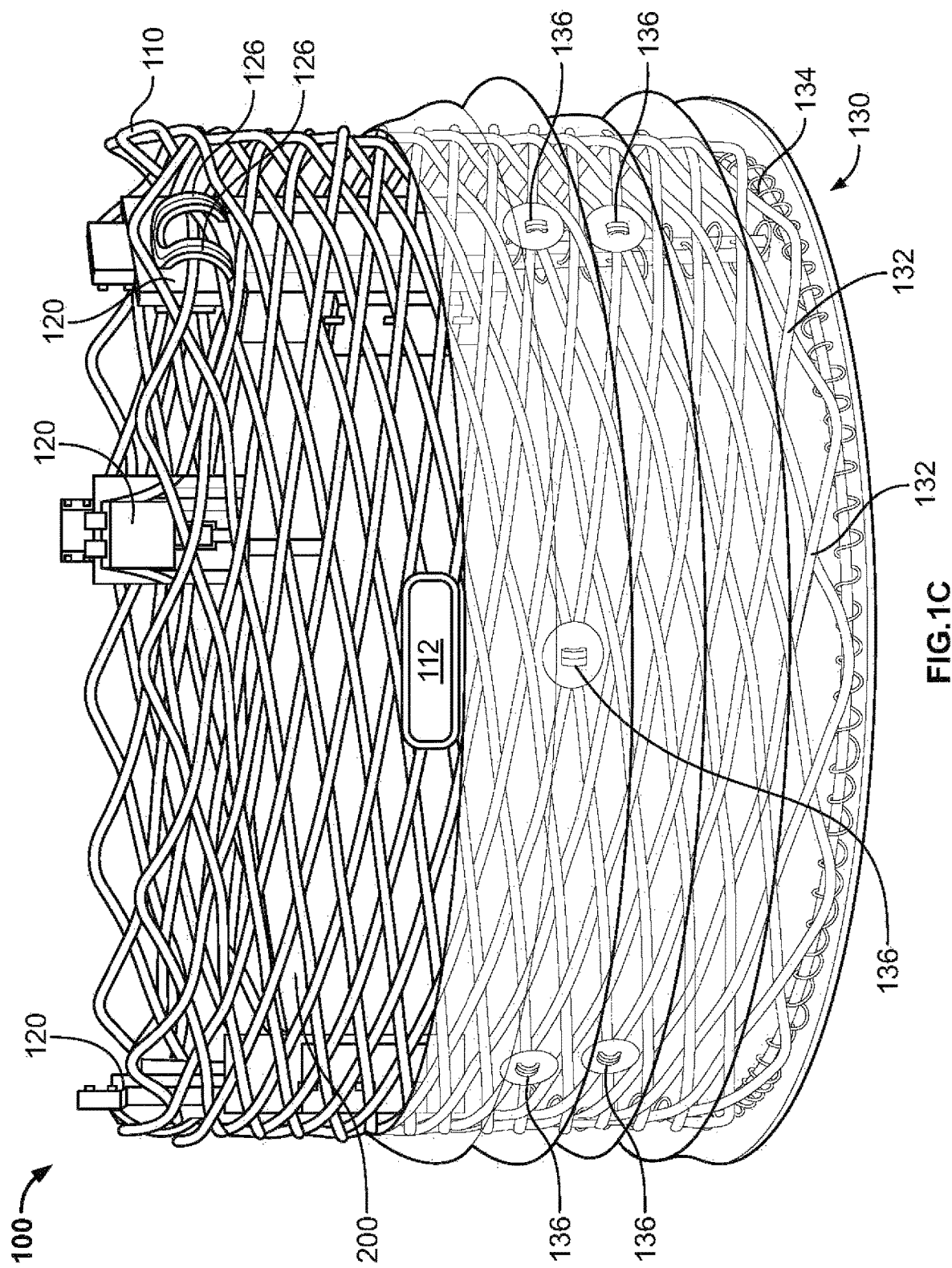
Figure 1D:
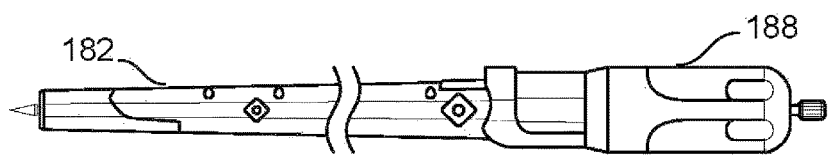
Figure 1E:
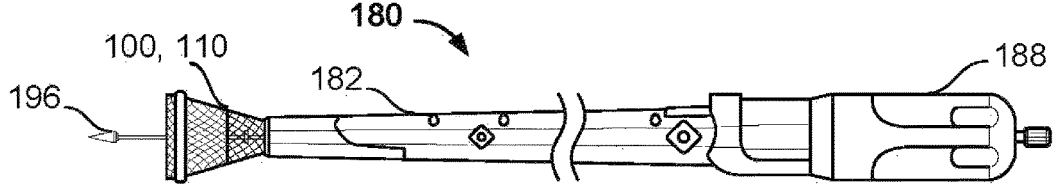
Figure 1F:
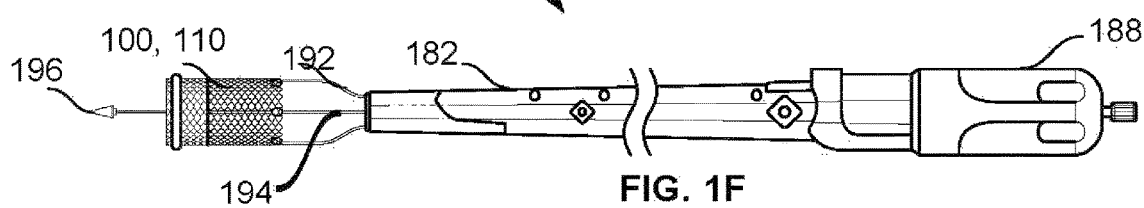
Figure 1G:
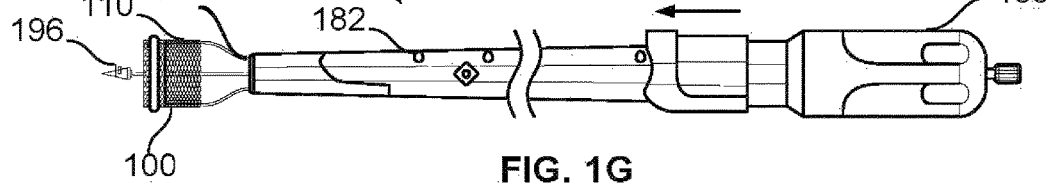
Figure 1H:
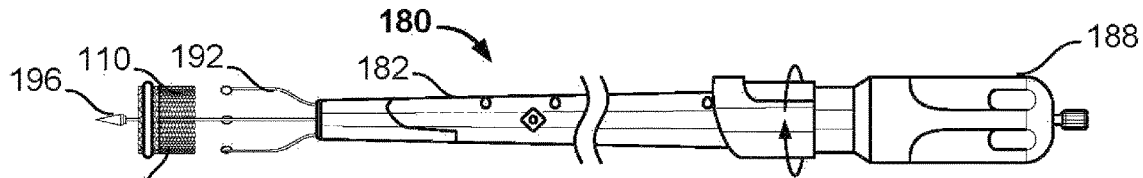
Figure 1I:
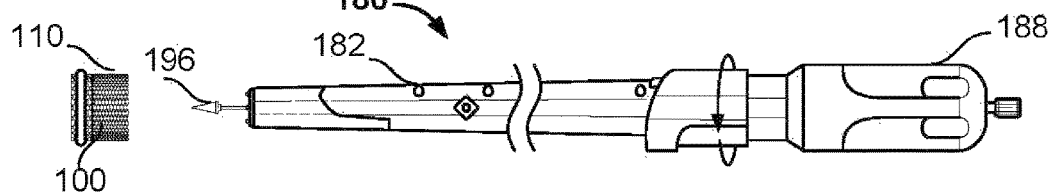

FIGS. 1A and 1B illustrate an exemplary prosthetic heart valve 100 provided herein. FIGS. 1A and 1B are perspective views of prosthetic heart valve 100 connected to a deployment device 190. FIG. 1C is a side view of prosthetic heart valve 100. As shown in FIGS. 1A-1C, prosthetic heart valve 100 includes an expandable member 110, three leaflets 200, three anchor elements 120 that secure sleeve portions 216 of leaflets 200 to expandable member 110, and a tubular seal 130 secured around a blood inflow end of prosthetic heart valve 100. To facilitate better understanding, FIG. 1A does not show components that are located underneath tubular seal 130, but FIG. 1B does show these components since tubular seal 130 can be made of transparent materials that would normally allow these components to be visible. Anchor elements 120 can include post leg compression elements 122 and clamping support structures 126 adapted to provide support along opposite sides of the sleeve portions 216. Expandable member 110 in FIGS. 1A-1I is a braided stent (which can also be described as a braided anchor element), which is adapted to transition between a restricted state having a smaller diameter and an expanded state having a larger diameter. Expandable member 110 can be self-expanding, mechanically expanded, or a combination thereof.

FIGS. 1D-1I depict how an exemplary heart valve delivery system 180 can deliver and deploy prosthetic heart valve 100 provided herein within a blood vessel. System 180 can include a sheath 182 for retaining prosthetic heart valve 100 with the expandable member 110 in a restricted state. Tubular seals provided herein can have a uniform thickness or a thickness that has a non-linear interface between an inflow end region and an outflow end region to provide a transition zone between a thinner outflow end region to the thicker inflow end region that facilitates loading of prosthetic heart valve 100 into sheath 182. For example, a substantially uniform thickness or a transition zone can reduce the probability for sections of the tubular seal to catch on an outer rim of sheath 182 during loading of prosthetic heart valve 100 in a restricted state. Additionally, tubular seals provided herein can allow for radial and/or axial expansion of the tubular seal in portions including non-elastic fibers, accordingly, a tubular seal used in prosthetic heart valves provided herein can have a non-expanded diameter that expands to the predetermined outer diameter of the expandable member and that stretches to an axially elongated but radially restricted configuration when prosthetic heart valve 100 is in a restricted state to further reduce the profile of prosthetic heart valve 100 within sheath 182.

Within sheath 182, anchor elements 120 (FIGS. 1A-1C) can be connected to pushing prongs 192 and a pull line 194 can be connected to a nose cap 196, or end cap, which is positioned at the end of sheath 182. As shown in FIGS. 1A and 1B, the pull line 194 can extend through expandable member 110 and through the valve opening between the leaflets 200. As shown by FIGS. 1D-1I, once a distal end of sheath 182 is delivered through the circulatory system to an appropriate location (e.g., within the heart), prosthetic heart valve 100 can be deployed. By advancing pushing prongs 192 and pull line 194 relative to sheath 182, prosthetic heart valve 100 can be pushed out of sheath 182. In some cases, expandable member 110 can self-expand upon exiting sheath 182. In some cases, expandable member 110 can self-expand to a first intermediate diameter, and system 180 can mechanically expand expandable member 110 to a larger deployment diameter. For example, anchor elements 120 can include a locking mechanism to clip a portion of expandable member when the expandable member 110 is expanded to a predetermined locking diameter. In some cases, system 180 can mechanically expand expandable member 110 to a predetermined locking diameter. In some cases, system 180 can compress expandable member 110 between pushing prongs 192 and nose cap 196 by moving pull line 194 relative to pushing prongs 192. The predetermined locking diameter can be adapted to set the diameter of prosthetic heart valve 100 during implantation. After prosthetic heart valve 100 is set, system 180 can move pull line 194 and nose cap 196 relative to pushing prongs 192 to move the end cap through the opening between leaflets 200 in prosthetic heart valve 100. Pushing prongs 192 can then be retracted from anchor elements 120 and retracted into sheath 182. In some cases, pushing prongs 192 can include a shape member material adapted to help radially expand expandable member 110 as the expandable member 110 exits sheath 182. A control handle 188 can be used to control the relative movements of sheath 182, pushing prongs 192, and pull wire 194. Prosthetic heart valves provided herein can be adapted to mitigate damage that may occur to valves during delivery and implantation.

In some cases, one or more radiopaque markers can be secured to prosthetic heart valves provided herein. As shown in FIGS. 1A-1C, expandable member 110 includes a radiopaque marker 112. Any suitable radiopaque material (such as platinum, palladium, gold, tantalum, or alloys thereof) can be used as the radiopaque material in radiopaque marker 112. One or more radiopaque markers can be used with an imaging system to help a physician ensure that a valve is set in an appropriate location. In some cases, prosthetic heart valves provided herein include at least three radiopaque markers.

Referring to FIGS. 1A and 1B, prosthetic heart valve 100 can include a plurality of leaflets 200. In some cases, as shown, prosthetic heart valve 100 includes three leaflets 200. In some cases, prosthetic heart valves provided herein can have any suitable number of leaflets, such as two, three, four, five, or more leaflets. In some cases, leaflets 200 are secured to one another. In some cases, leaflets 200 can be secured to one another by a suture (not shown) or a plurality of sutures. Leaflets 200 can be sutured alongside edges of a body portion of each leaflet. In some cases, prosthetic heart valves provided herein can include a single line of sutures, which can be adapted to minimize leaks, minimize the width of a seam, and/or minimize the profile of a replacement heart valve during a percutaneous insertion. In some cases, prosthetic heart valves provided herein can include multiple lines of sutures.

Expandable member 110 can have any suitable structure, arrangement, or material. In some cases, expandable member 110 can include a braided wire stent. For example, U.S. Publication Number 2005/0143809, titled, "Methods and Apparatus for Endovascularly Replacing a Heart Valve,"

and filed on Nov. 5, 2004, which is herein incorporated by reference for its disclosure of possible structures and materials for a braided wire stent, discloses a braided wire stent. In some cases, expandable member 110 includes a shape memory material (e.g., a nickel-titanium alloy or a cobalt-chromium alloy).

Figure 2B:
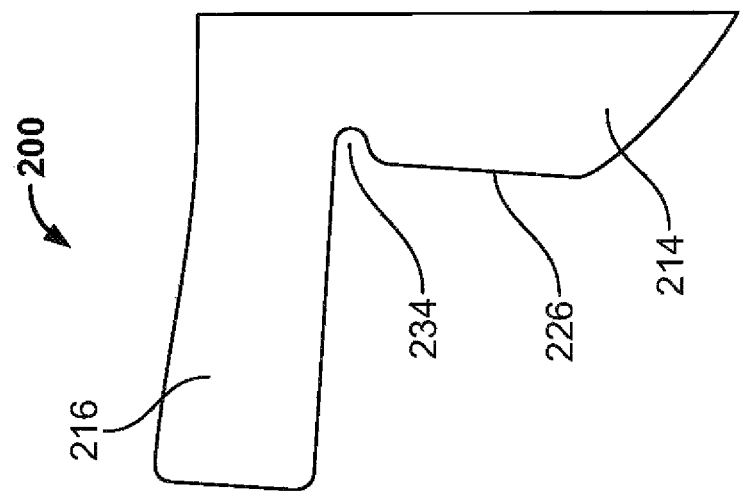
FIGS. 2A-2C illustrates an exemplary leaflet, which can be used in prosthetic heart valves provided herein.
Figure 2A:
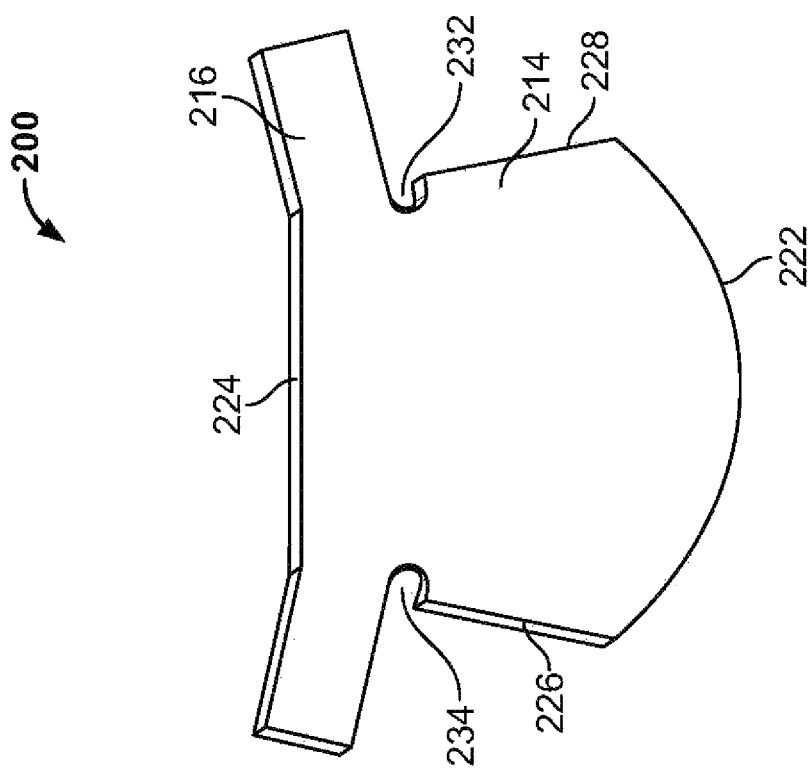
Figure 2C:
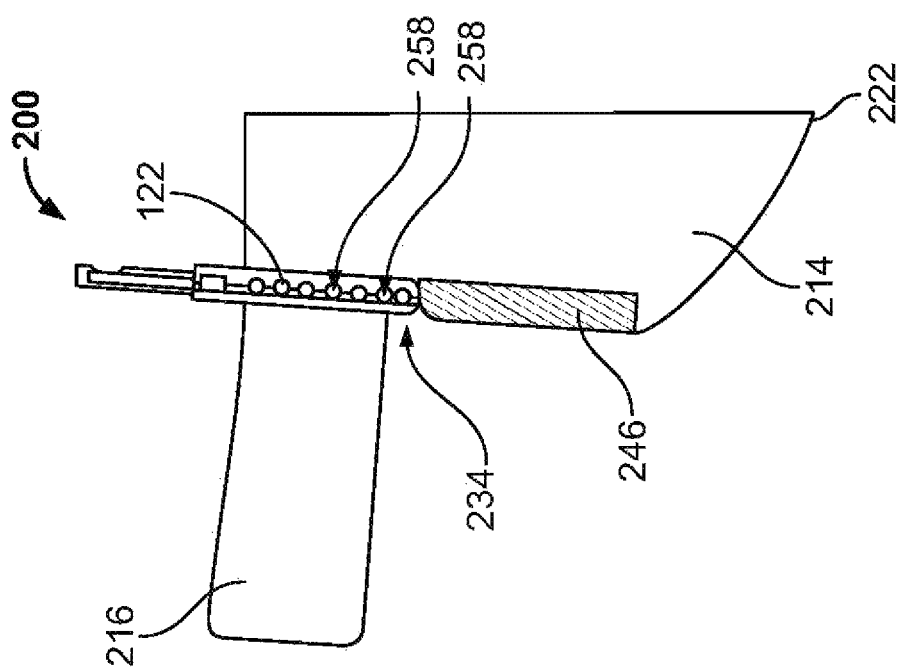

FIGS. 2A-2C provide illustrations of an exemplary leaflet 200 that includes a body portion 214 and sleeve portions 216. In some cases, body portion 214 has a bottom edge 222, a first side edge 226, a second side edge 228, and a free edge 224. Leaflet 200 further includes a front (i.e., a side facing the blood inflow end of a prosthetic heart valve), a back (i.e., a side facing the blood outflow end), a first side adjacent to the first side edge 226, and a second side adjacent to the second side edge 228. In some cases, the front of leaflet 200 has a different texture than the back. In some cases, the back or front can have a non-textured or textured surface to mitigate calcium buildup on the surfaces. For example, in some cases, the back of leaflet 200 may be prone to calcium build due to a cusp-shaped, concave surface, thus it can be beneficial to have a textured surface on the back of leaflet 200 to mitigate calcification issues. Leaflets can be made of various synthetic or non-synthetic materials. In some cases, the leaflet 200 is made from tissue obtained from an animal, e.g., a pig or a cow. In some cases, leaflet 200 is made from bovine pericardium. In some cases, leaflets 200 can be made from a synthetic polymers or composites. Leaflets 200 can be assembled into a heart valve by aligning the opposite side regions of at least two adjacent leaflets 200 and stitching the leaflets 200 together along stitch line 246, which is shown in FIG. 2C.

Still referring to FIGS. 2A-2C, leaflet 200 defines at least one notch 232, 234 between at least one of the two side edges 226, 228 and a corresponding adjacent sleeve portion 216. Each notch 232, 234 can be located along side edges 228, 226 at a location adjacent to the sleeve portions 216, e.g., at an "armpit" of leaflet 200 as depicted in FIGS. 2A and 2B. In some cases, leaflet 200 can define a notch along the length of side edges 228, 226. In some cases, a notch can be defined along sleeve portion 216. In some cases, multiple notches can be located along sleeve portion 216, side edges 228, 226, and/or at the armpit of the leaflet 200.

As shown in FIGS. 2A and 2B, body portion 214 of leaflet 200 has a conical frustum shape defined by bottom edge 222, first side edge 226, second side edge 228, and free edge 224. Other suitable shapes for the body portion can include, but are not limited to, for example, a generally square, rectangular, triangular or trapezoidal shaped body portion.

The sleeve portions 216, as shown in FIGS. 2A-2C, can extend outwardly from the body portion 214 of the leaflet 200. Each sleeve portion 216 can oriented at an angle relative to a portion of the body portion, e.g., free edge 224 of body portion 214. Sleeve portions 214, as shown, can be generally rectangular-shaped extensions with lateral free ends. In some cases, sleeve portions 214 can have rounded free ends.

Still referring to FIGS. 2A-2C, notches 232, 234 can be generally U-shaped. Other suitable notch shapes can include, but are not limited to, a V-shaped, rectangular-shaped, oval-shaped, and circular notch. In some cases, notches 232, 234 can have rounded edges to smooth the transition between a notch 232, 234 and side edges 228, 226 of leaflet 200. Notches 232, 234 can have a length dimension that can range from about 0.5 millimeters (mm) to about 4 mm (from about 0.02 inches to about 0.20 inches).

Referring to FIG. 2C, notches 232, 234 can be shaped and sized to accommodate attachment of post leg compression elements 122. Post leg compression elements 122 can be a part of anchor elements 120 (shown in FIGS. 1A-1C) that compress and restrain sleeve portions 216 along the same line as the stitch line 246. As shown in FIG. 2C, suture 258 can be used to apply an appropriate and consistent compressive force between post leg compression elements 122 in order to prevent leakage through sleeve portions 216 of leaflets 200. Since suture 258 pass through notches 232, 234, it does not need to pass through body portion 214 at or near the armpit of leaflet 200. Sutures that pierce the body portion at or near the armpit of the leaflet can pull, stretch and abrade surrounding tissue areas, creating stress concentrations at or near the armpit of the leaflet. These stress concentrators can result in tears forming in the leaflet. The use of notches 232, 234 with post leg compression elements 122, therefore can minimize potential heart valve tearing that might be caused by sutures at or near the armpit location. Notches 232, 234 create enlarged openings that suture 258 can pass therethrough without pulling or stretching the adjacent tissue. Accordingly, a notched leaflet 200 can improve valve opening capabilities and the reliability of prosthetic heart valves provided herein.

Figure 3:
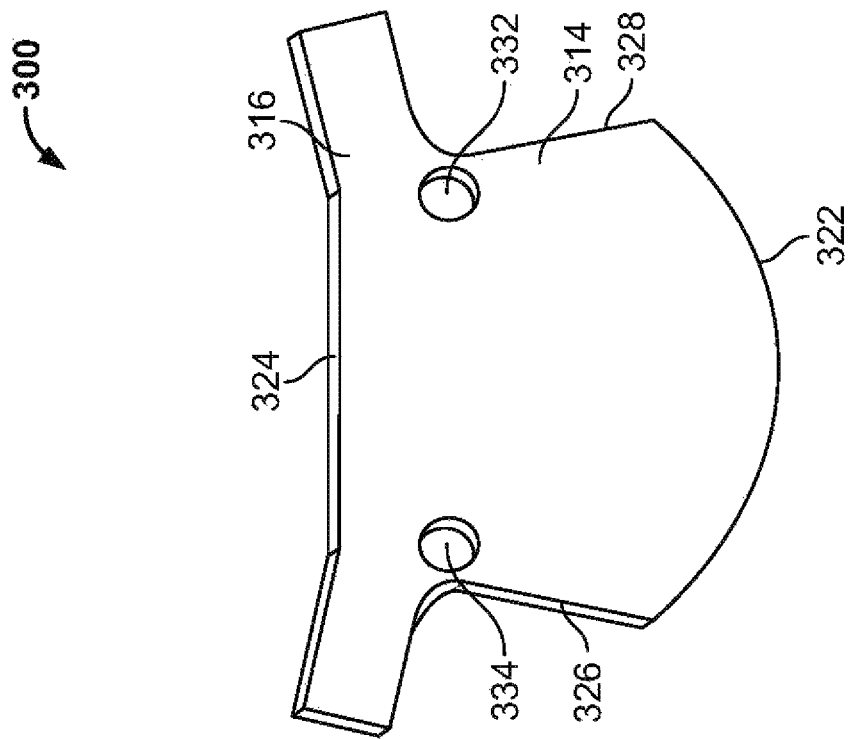
FIG. 3 illustrates another exemplary leaflet, which can be used in prosthetic heart valves provided herein.

FIG. 3 illustrates another exemplary leaflet 300, which can be used in prosthetic heart valves provided herein. As shown in FIG. 3, leaflet 300 can include a body portion 314 and at least two opposite sleeve portions 316. The body portion 314 can be defined by at least two side edges 326, 328 adjacent each sleeve portion 316. Leaflet 300 can define two apertures 332 and 334. Each aperture 332, 334 can be positioned adjacent side edges 326, 328 and the corresponding adjacent sleeve portion 316.

Still referring to FIG. 3, body portion 314 has a bottom edge 322, a first side edge 326, a second side edge 328, and a free edge 324. Leaflet 300 further includes a front, a back, a first side adjacent to the first side edge 326, and a second side adjacent to the second side edge 328. Leaflets 300 can be assembled into a heart valve by aligning the opposite side regions of at least two adjacent leaflets 300 and stitching the leaflets 300 together along stitch line 246, as shown in FIG. 2C.

As shown in FIG. 3, leaflet 300 defines apertures 332 and 334 adjacent side edges 328, 326 and adjacent one of the sleeve portions 316. Apertures 332 and 334 can be generally circular in shape. Other suitable aperture shapes can include, but are not limited to, for example, a rectangular, oval, triangular, or diamond-shaped aperture. In some cases, apertures 332, 334 can have a length dimension or a diameter from about 0.5 mm to about 4 mm (or about 0.02 inches to about 0.20 inches). In some cases, one or more apertures 332, 334 can be located in the side edges 328, 326 and/or the sleeve portions 316 of the leaflet 300. In some cases, multiple apertures can be located in a region that is adjacent to the side edges 328, 326 and the sleeve portions 316.

Apertures 332, 334 in the leaflets 300 can allow one leaflet to be secured to an adjacent leaflet. Similar to the notches discussed above, apertures 332 and 334 can be shaped and sized to accommodate attachment of post leg compression elements 122. Referring back to FIGS. 1A-1C, post leg compression elements 122 can be a part of anchor elements 120 that compress and restrain sleeve portions 216 along the same line as the stitch line 246. A suture 258 can be used to apply an appropriate and consistent compressive force between the post leg compression elements 122 in order to prevent leakage through sleeve portions 216 of the leaflets 200. As already discussed herein, sutures that pierce the body portion 214 at or near the armpit of the leaflet can create stress concentrations at or near the armpit of the leaflet that may result in tearing. Apertures 332 and 334 and post leg compression elements 122, however, can minimize this potential tearing caused by sutures near the armpit location by being positioned proximate to the post leg compression elements near the armpit. Apertures 332, 334 create enlarged openings that allow suture 258 to pass therethrough without pulling or stretching adjacent tissue areas. Accordingly, leaflets 300 used in prosthetic heart valves provided herein can improve the reliability of prosthetic heart valves.

FIGS. 4A-4G depict how leaflets 200 can be connected (or jointed) with an improved stitch discussed herein. As shown, stitch 446 can be a single continuous line stitch traveling along a stitch line in a forward direction and back in a reverse direction. In some cases, stitch 446 can run along a leaflet from a bottom edge to a side edge of the leaflet (e.g., bottom edge 222 to side edge 226 of leaflet 200 in FIG. 2A-2B). In some cases, stitch 446 can run from a side edge to a notch of a leaflet (e.g., side edge 226 to notch 234 of leaflet 200 in FIG. 2A-2B).

As shown in FIGS. 4D-4G, stitch 446 can include a plurality of perpendicular loop segments 434 extending through an aperture in the two leaflets, around outer side edges of the two attached leaflets, and back through the aperture. Stitch 446 can include a plurality of parallel segments 436 extending between adjacent apertures along the stitch line. Stitch 446 can include two perpendicular loop segments 434 extending through apertures formed in the stitch line. In some cases, a first perpendicular loop segment 434 for a first aperture in the stitch line is formed when the stitch is formed in the forward direction and a second perpendicular loop segment 434 for the first aperture is formed in the reverse direction. In some cases, parallel segments 436 made in a forward direction alternate between opposite sides of the two leaflets between each aperture in the stitch line. In some cases, parallel segments 436 made in a reverse direction are formed on an opposite side of the two leaflets from parallel segments 436 made in a forward direction. In some cases, opposite parallel segments 436 made in the forward and reverse directions can provide a continuous compressive force along the entire length of the stitch line. Perpendicular loop segments 434 can provide compressive force to reinforce a seal formed between the two leaflets along the stitch line.

Stitch 446 can include any appropriate number of perpendicular loop segments formed through any appropriate number of apertures. As shown, stitch 446 includes six perpendicular loop segments formed through six apertures (two perpendicular loop segments per aperture). In some cases, stitch 446 can include up to twelve perpendicular loop segments formed through six or more apertures. In some cases, a stitch connecting side edge segments of leaflets can be formed using between 3 and 20 apertures and include between 3 and 40 perpendicular loop segments. In some cases, apertures can be positioned from about 0.2 mm to about 10 mm apart (or about 0.008 inches to about 0.4 inches apart). In some cases, apertures can be positioned from about 0.2 mm to about 10 mm (or about 0.008 inches to about 0.4 inches) away from the side edges of the leaflets.

Figure 4A:
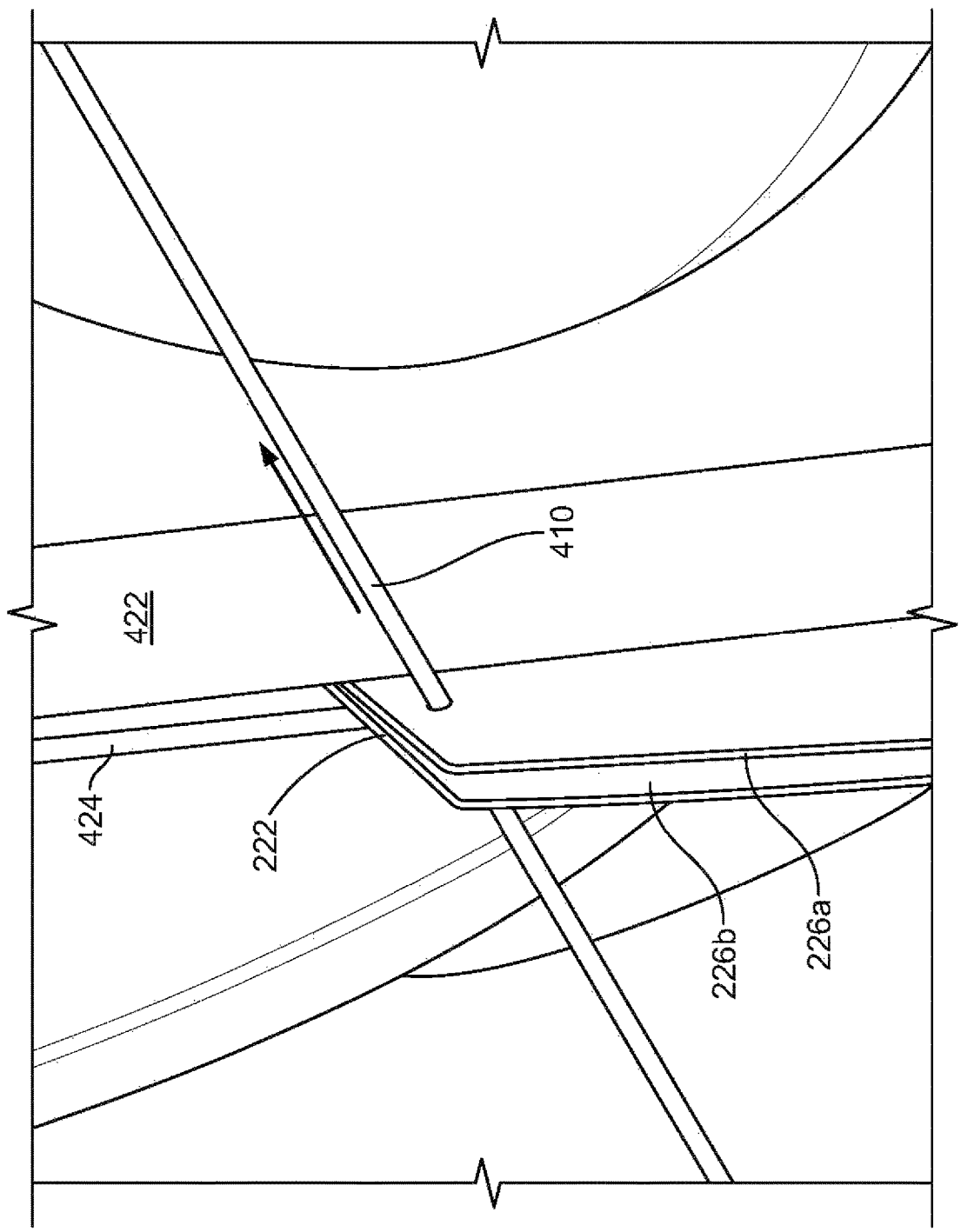
Figure 4B:
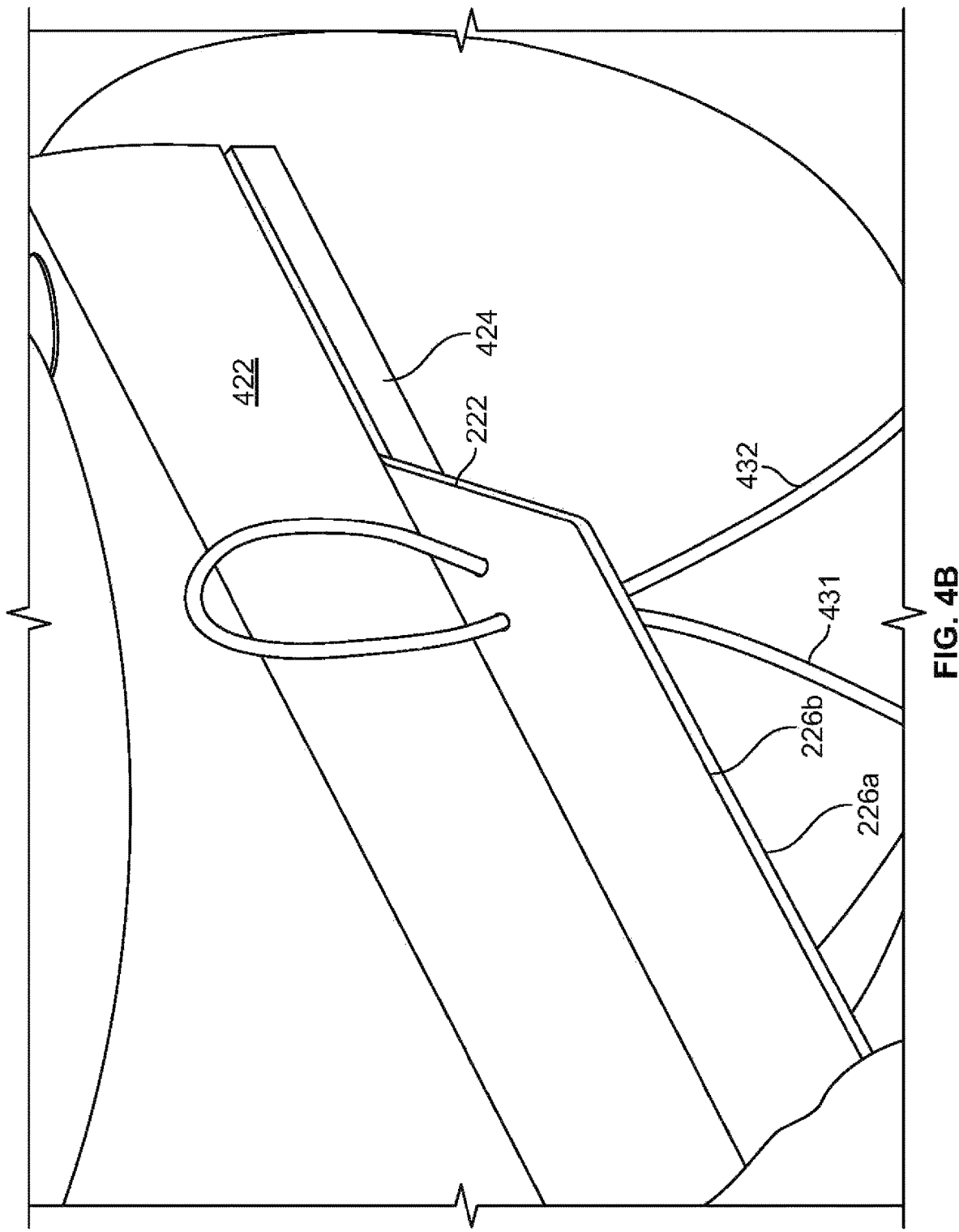
Figure 4D:
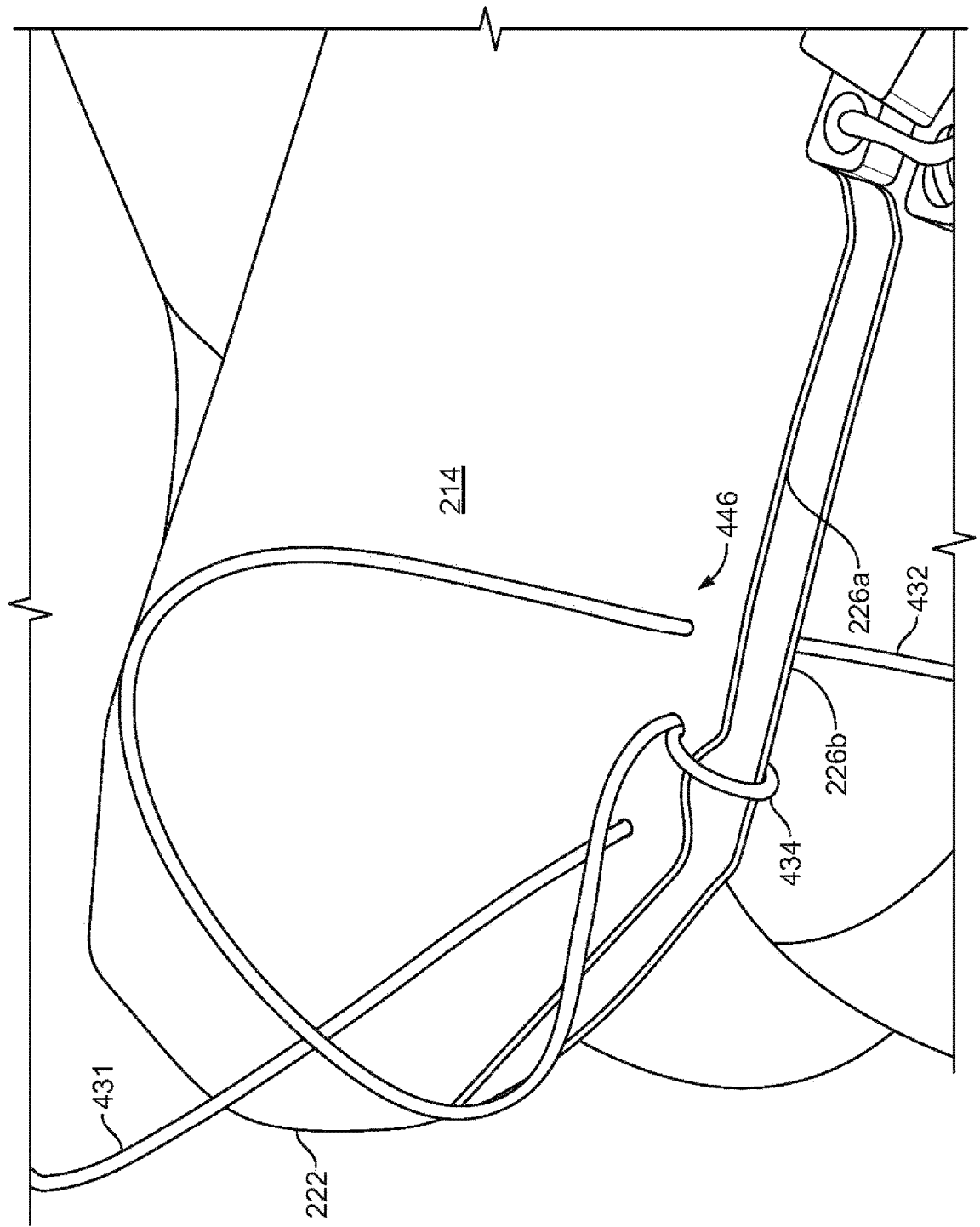
Figure 4E:
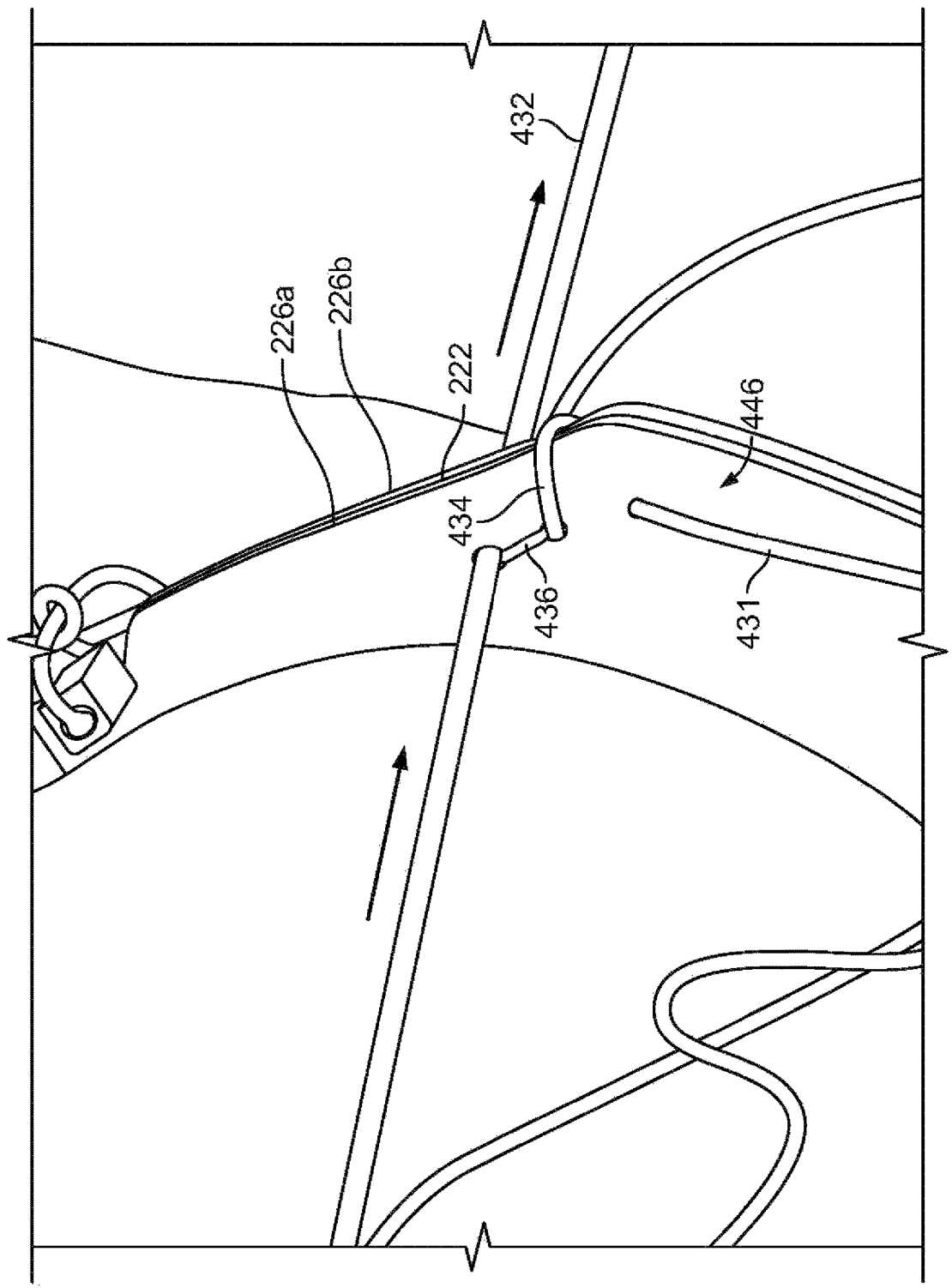
Figure 4F:
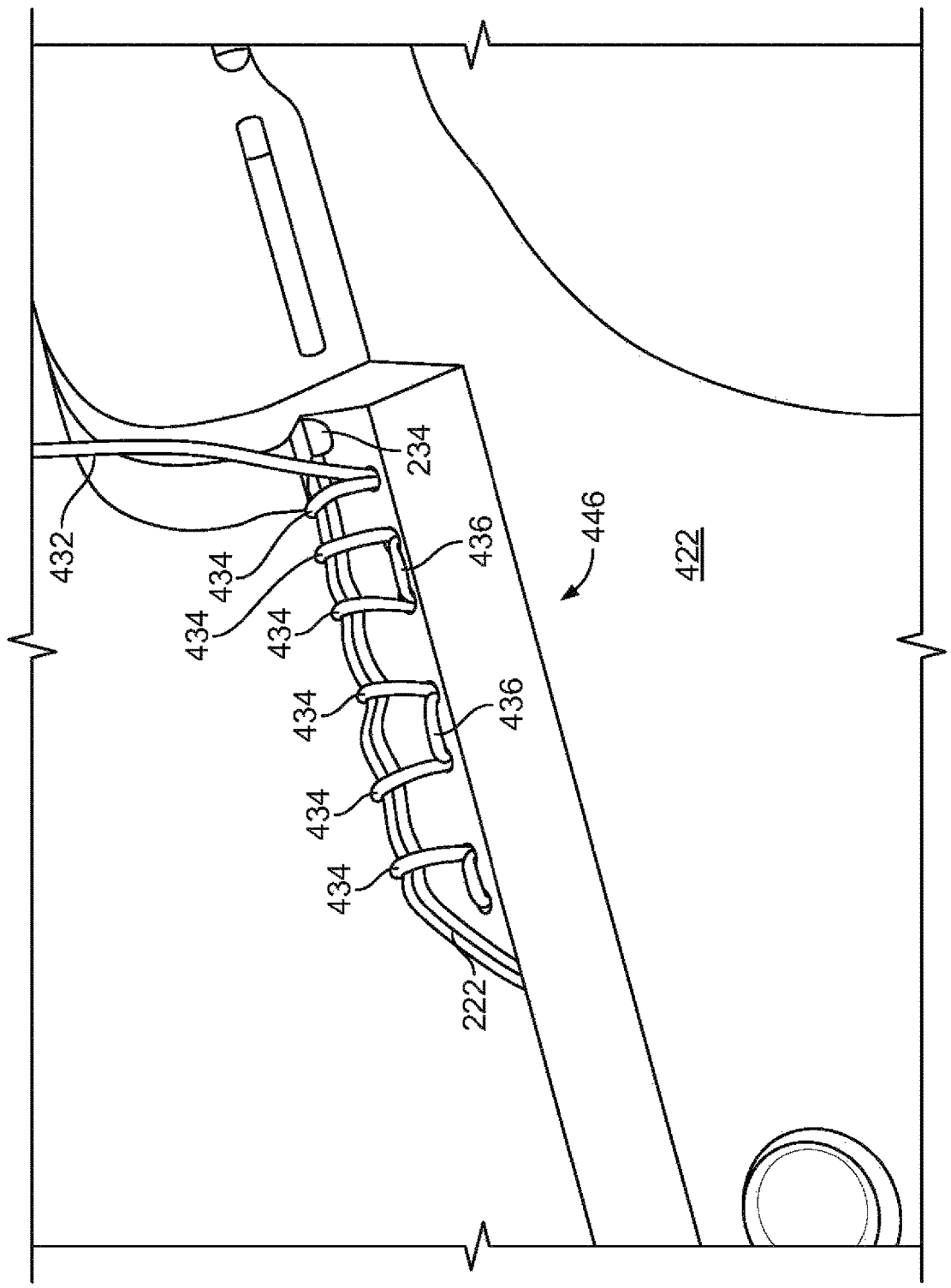
Figure 4G:
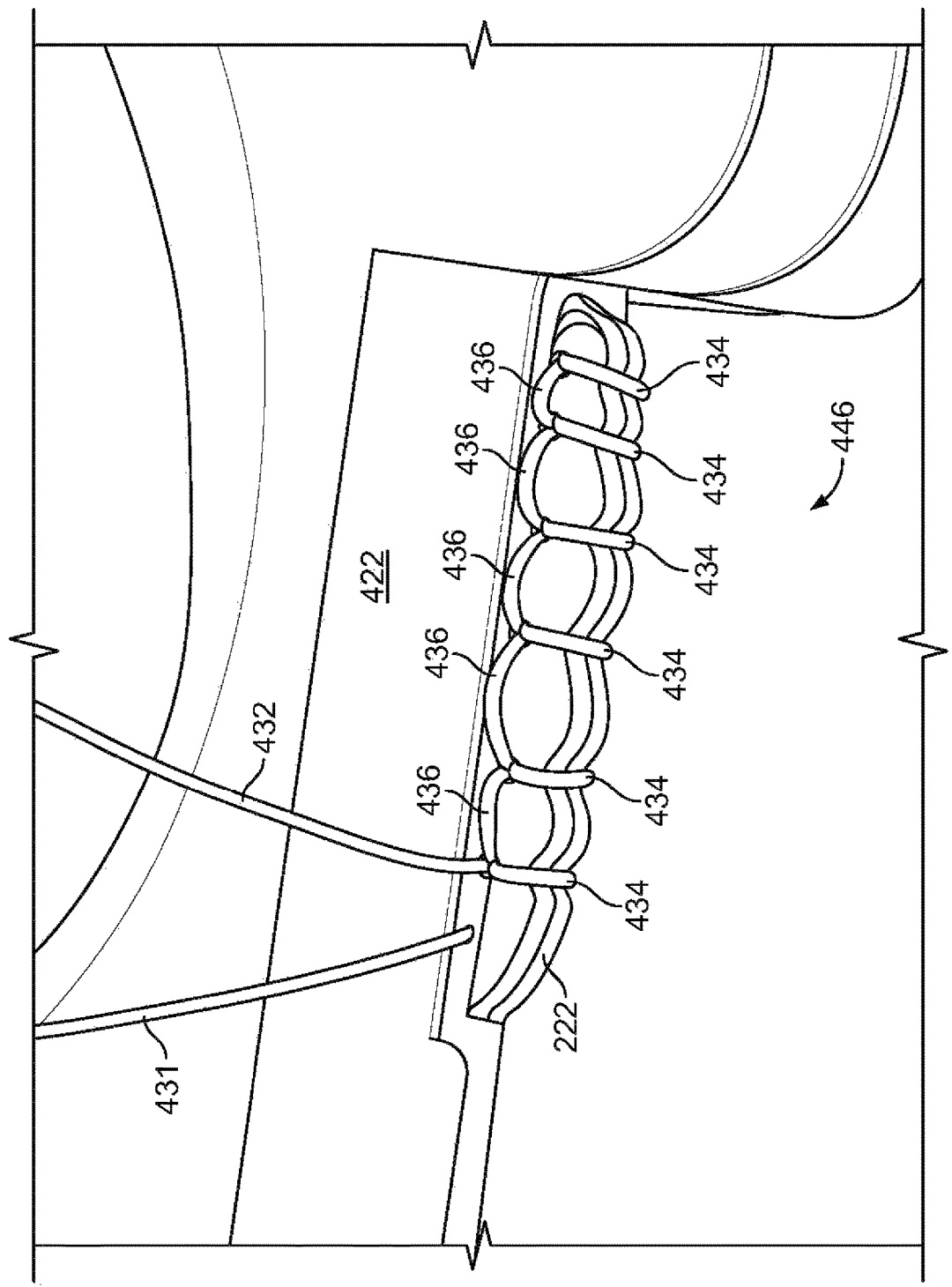

Stitch 446 can be formed in a process depicted in FIGS. 4A-4G. As shown in FIG. 4A, a thread needle 410 can be passed through aligned leaflet side edges 226a and 226b to create a first aperture at a location near bottom edges 222, e.g., a location approximately 1 mm from the bottom edges 222. The leaflet side edges 226a and 226b can be retained in a desired configuration by clamping the leaflets between clamp sides 422 and 424. Needle 410 pulls a leading end 431 of a thread 432 through the first aperture. As shown in FIG. 4B, needle 410 can then form a second aperture adjacent to the first aperture along the stitch line (towards the leaflet sleeve portion) about 0.5 mm away from the first aperture to pull leading end 431 of thread 432 through the second aperture to form a first parallel segment. As shown in FIG. 4C, a perpendicular loop segment 434 can be made by guiding needle 410 around the leaflet side edges and reenter the second aperture from a backside. Thread 432 can be pulled through the second aperture until it sits firmly against the leaflet material (e.g., leaflet pericardium tissue). FIG. 4D shows a second parallel segment, which can be made by pushing needle 410 through leaflet tissue along the stitch line to form a third aperture approximately 1 mm from the second aperture (towards the sleeve segments of the leaflet). As shown in FIG. 4E, a second perpendicular loop segment 434 can be formed by again having needle 410 loop around the leaflet side edges and reenter the third aperture through the backside. This is repeated up to notch 234 to form a total of six parallel segments 436 and six perpendicular loop segments 434 in a forward direction, as shown in FIG. 4F. The stitch pattern can then be repeated in a reverse direction towards the bottom edges 222 of the leaflets through the previously formed apertures. Accordingly, each aperture can include two perpendicular loop segments 434 and parallel segments on the opposite sides can be formed from the parallel segments that were created in the forward direction, as shown in FIG. 4G. The method and stitches depicted in FIGS. 4A-4G can be applicable to leaflets 200, 300 discussed herein.

Stitch 446 and other stitches provided herein can improve the reliability of a seal formed along a stitch line, create fewer apertures through the leaflets, and simplify the stitching operation. Having fewer apertures can help minimize the occurrence of blood leakage through the apertures. The single continuous line of stitch 446 using a single row of apertures can minimize a width of a side edge portion needed to form a continuous seal along the side edges of the leaflets, thus providing a reduced restricted profile for prosthetic heart valves provided herein. For example, U.S. Pat. No. 8,778,020 describes a variety of ways that leaflets can be sutured together using combinations of whip stitches and running stitches, but these stitches require additional apertures and multiple lines. Perpendicular loop segments 434 can stitch a plurality of leaflets together, similar to the whip stitches discussed in U.S. Pat. No. 8,778,020. Parallel segments 436 can secure valve leaflets to one another, similar to the running stitches discussed in U.S. Pat. No. 8,778,020. Although stitch 446 can provide an improved attachment between side edges of leaflets in prosthetic heart valves provided herein, some embodiments of prosthetic heart valves provided herein can use other stitch patterns, such as those described in U.S. Pat. No. 8,778,020, which is hereby incorporated by reference.

Important characteristics of a suture thread can include, but are not limited to, adequate tensile strength, abrasion resistance and creep rupture resistance characteristics that allow the device to be delivered into and sustain implantation within a human anatomy. The thread used for suturing together portions of the heart valve, e.g., side edges of the leaflets, can be composed of biocompatible materials that include, but are not limited to, polyethylene such as ultra high molecular weight polyethylene (UHMWPE), polyester (PET), and a combination thereof.

Referring back to FIGS. 1A-1C, tubular seal 130 of prosthetic heart valve 100 can be secured to bottom edges 222 (FIG. 2A) of body portion 214 of leaflet 200 by a circumferential running stitch 134. In some cases, tubular seal 130 can be secured to expandable member 110 by fasteners, such as grommets 136, and extended around the outside of expandable member 110 to provide a seal that minimizes blood leakage around the leaflets 200 of an implanted prosthetic heart valve 100. The structure and materials of tubular seal 130 are further discussed with reference to FIGS. 6 and 7A-7E.

Figure 5A:
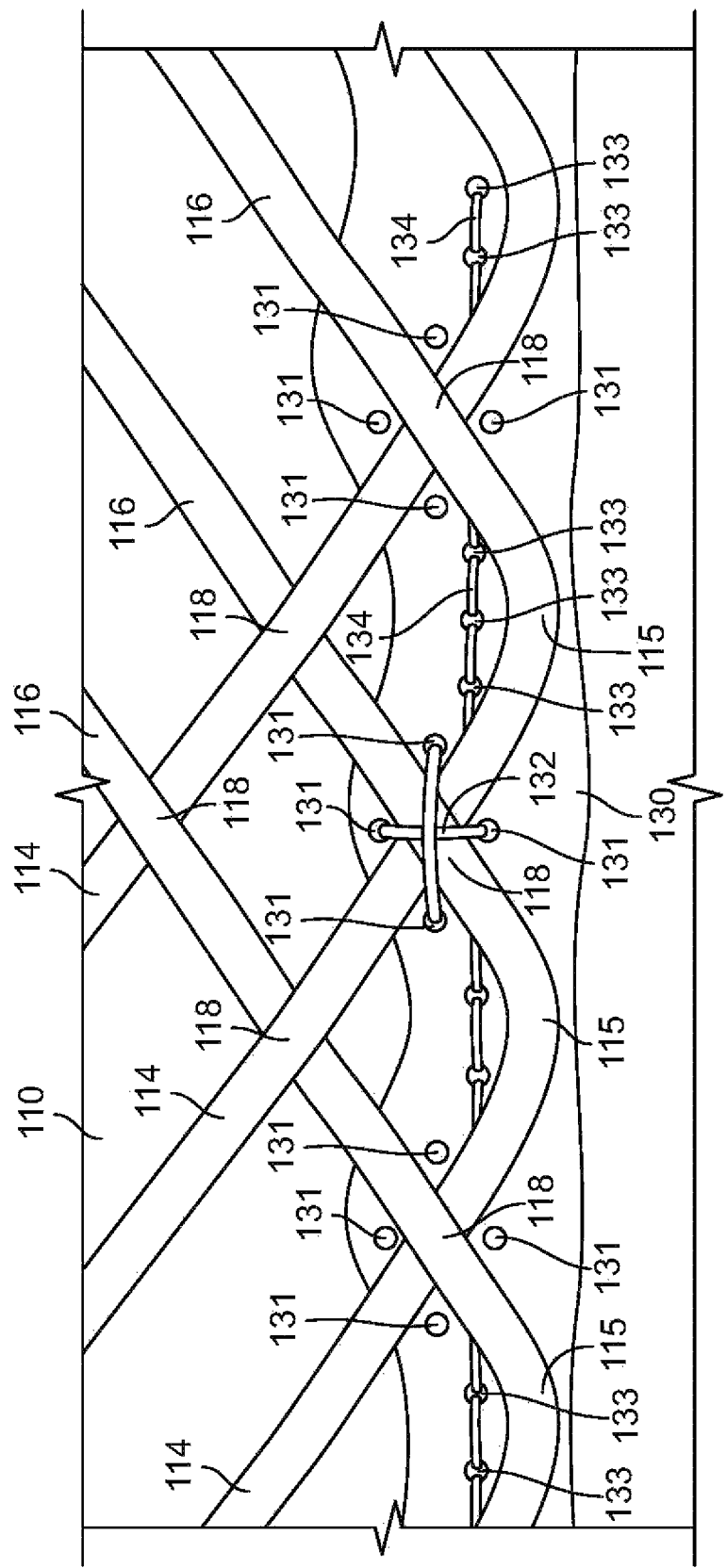
FIGS. 5A-5C illustrate a cross stitch provided herein for connecting a seal to a braided stent in an exemplary prosthetic heart valve provided herein.
Figure 5B:
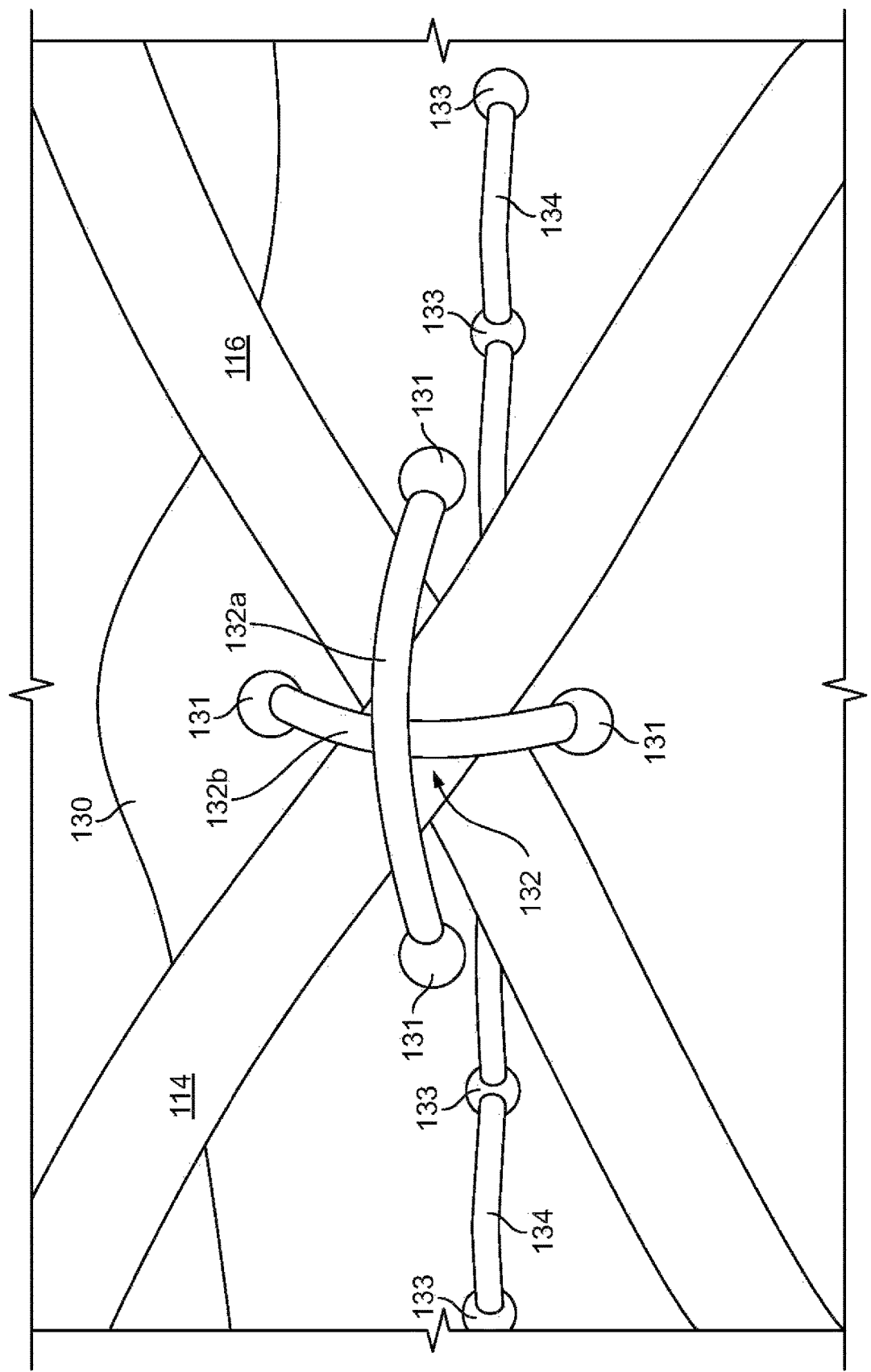
Figure 5C:
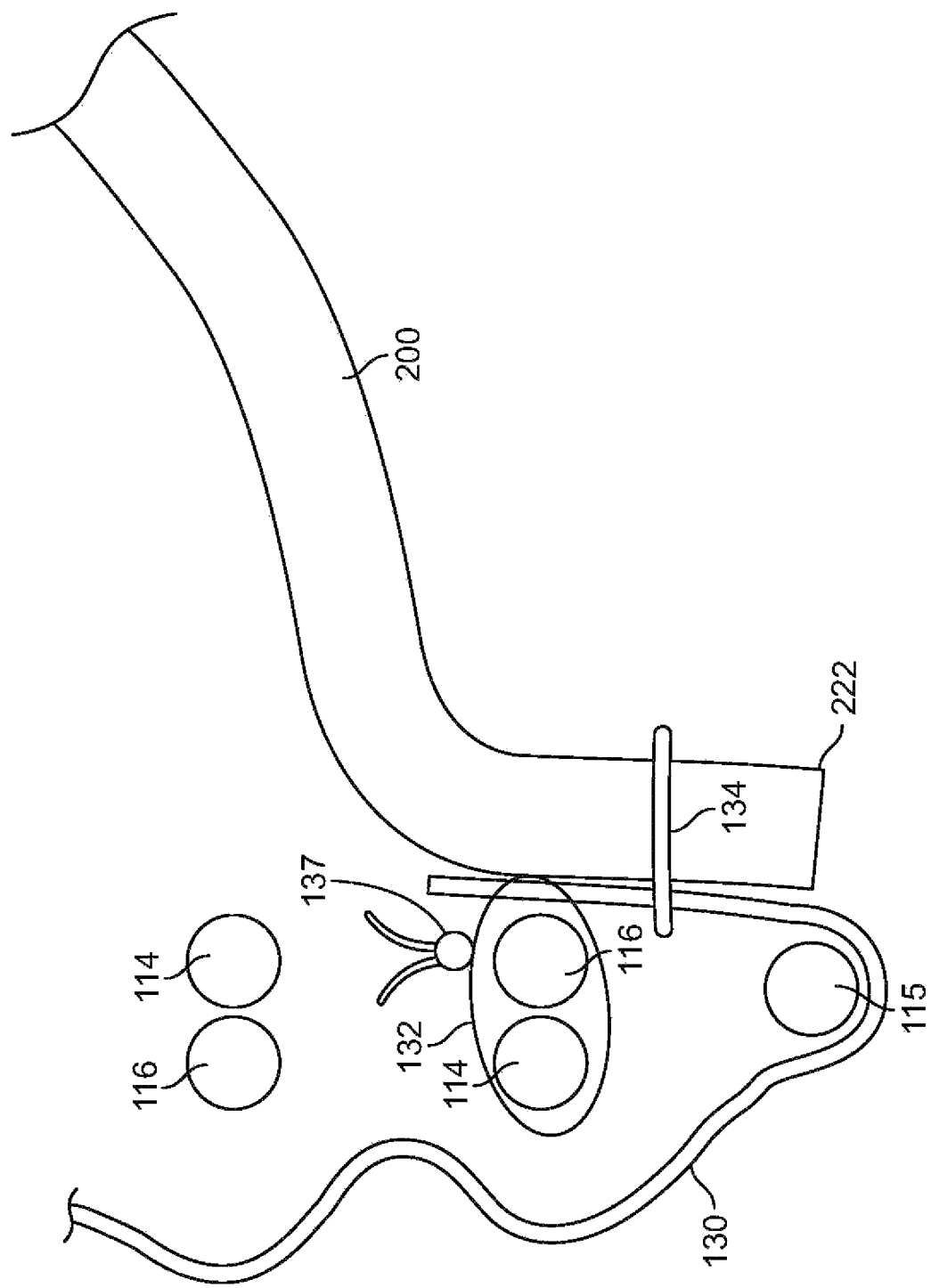

FIGS. 5A-5C provide an improved tubular seal stitching pattern can include a cross stitch 132 between tubular seal 130 and expandable member 110. For example, a blood inlet side of expandable member 110 (e.g., braided anchor element) can be secured to a portion of the tubular seal having the woven fabric by a plurality of stitches (e.g., a plurality of cross stitches securing the seal to two crossing members of a braided stent). FIGS. 5A-5C illustrate how the tubular seal 130 can be secured to the expandable member 110, e.g., a braided stent, by a plurality of cross stitches connecting the tubular seal 130 to a pair of overlapping wire members of the braided stent. As shown in FIGS. 1A-1C and 5A-5C, expandable member 110 can be a braided stent including one or more wires having a first set of segments 114 extending helically in a first direction and a second set of segments 116 extending helically in a second direction such that the first set of segments 114 cross the second set of segments 116 at intersection points 118. As shown, one or more wires can have inflow crowns 115 at an end of the braided stent where the wires transition from first segments 114 to second segments 116. In some cases, cross stitches 132 secure tubular seal 130 at an intersection 118 to two crossing segments 114, 116 of the braided stent. A separate circumferential running stitch 134 can be inserted into preformed apertures 133 to secure the adaptive seal to bottom edges 222 of leaflets 200 shown in FIGS. 2A and 2C. Cross-stitches around the intersections 118 can increase the strength of an attachment of tubular seal 130 to the expandable member 110 while also allowing for improved load transfer to the expandable member 110. In some cases, the cross stitches secure tubular seal 130 at intersections 118 located immediately above (proximal) the inflow crowns 115. Cross stitches 132 can be formed by passing two stitches 132a, 132b of a suture in orthogonal directions over the intersections 118 and through the tubular seal 130. In some cases, preformed apertures 131 for cross stitch 132 can be formed in the tubular seal 130. In some cases, a portion of the tubular seal 130 that is sutured by cross stitch 132 includes an internal fabric, such as those discussed below. Each cross stitch 132 can be knotted independently. As shown in FIG. 5C, cross stitches 132 each include a separate knot 137. Additionally, cross stitches 132 can be arranged to not pass through leaflets 200. Cross stitches 132 can be repeated at a plurality of intersections 118 (FIG. 5A) circumferentially around an inflow end of a prosthetic heart valve provided herein such that an entire circumference of tubular seal 130 is securely attached. In some cases, each intersection 118 immediately adjacent to inflow crowns 115 is sutured to tubular seal 130 via a cross stitch provided herein. The tubular seal stitching pattern provided herein can increase the strength of the attachment between the tubular seal 130 and the expandable member 110 while also allowing for improved load transfer to the expandable member 110 through the use of the plurality of cross stitches.

Referring back to FIGS. 1A-1B, tubular seal 130 of prosthetic heart valve 100 can have various suitable structures, arrangements, or materials that allow tubular seal 130 to be secured to leaflets 200 within prosthetic heart valve 100. Various suitable structures, arrangements, or materials of tubular seal 130 can be used to allow tubular seal 130 to extend around the outside of expandable tubular member 110 to prevent blood leakage around leaflets 200.

Figure 6:
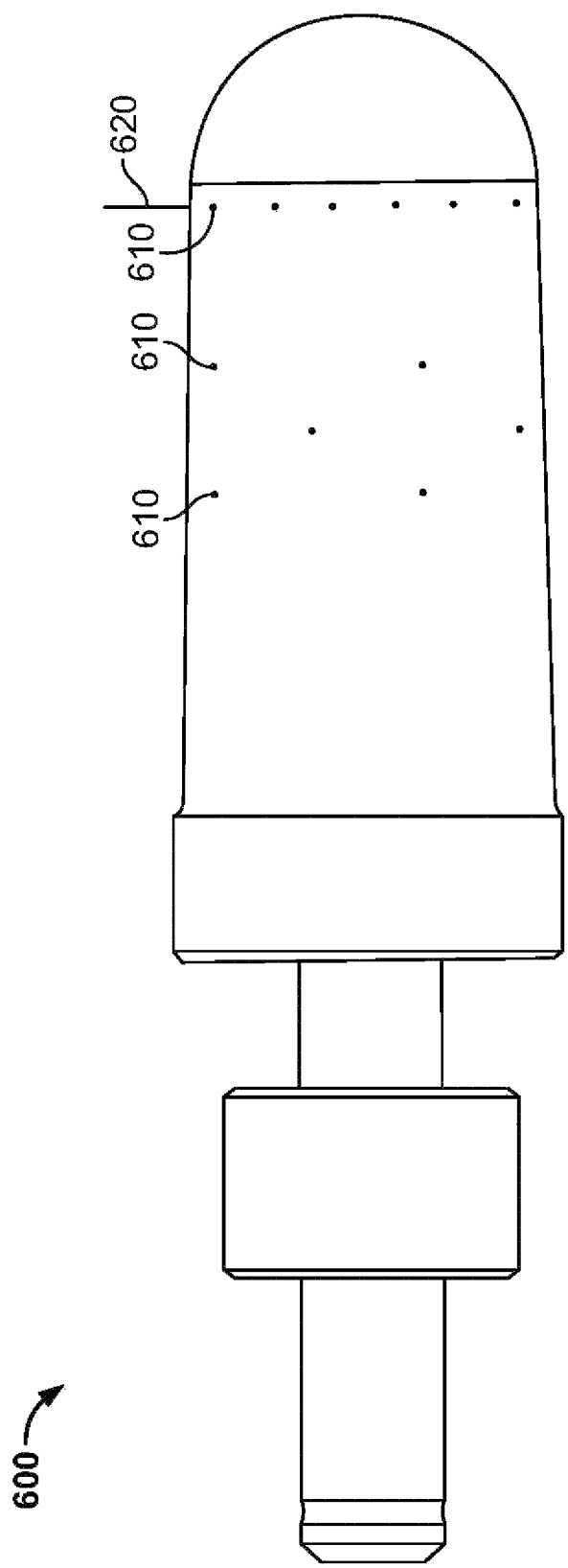
FIG. 6 depicts an apparatus that can be used to form a tubular seal provided herein.

FIG. 6 shows an exemplary mandrel 600 that can be used to construct a tubular seal. The mandrel 600 includes a taper which results in a tubular seal having a slightly smaller diameter proximal end compared to the diameter of the distal end. In some cases, the diameter of the proximal end can include a diameter reduction of about 3% to about 30% as compared to the diameter of the distal end. The taper allows the tubular seal to be removed from the mandrel with relative ease upon completion of the fabrication process. The smaller proximal diameter of the tubular seal tends to cause the proximal projections to lie more firmly against an anchor element of the replacement heart valve. In some cases, the surface of the mandrel may be textured to create a tubular seal with a reduced contact area. In some cases, the mandrel can be textured using a bead blasting process. In combination with the selection of a relatively hard outer layer, a textured seal surface is believed to result in a lower friction surface.

Figure 7A:
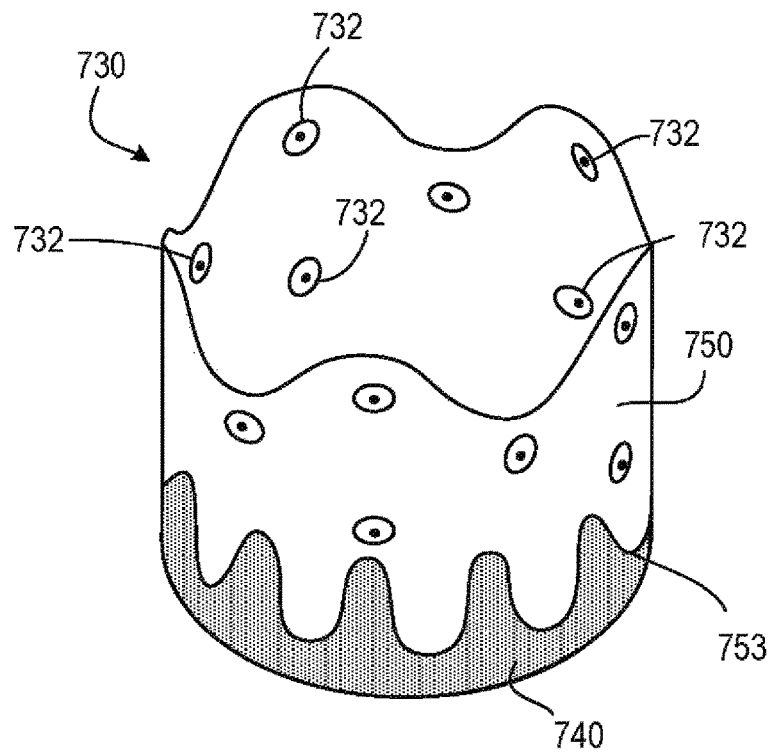
FIGS. 7A-7G illustrate exemplary tubular seals that include a fabric having a non-linear edge positioned within a polymeric web or matrix in a prosthetic heart valve provided herein.
Figure 7B:
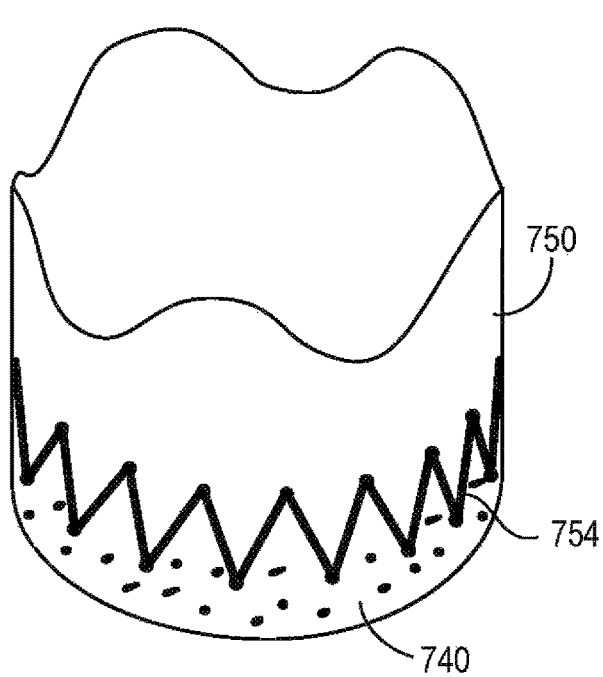
Figure 7C:
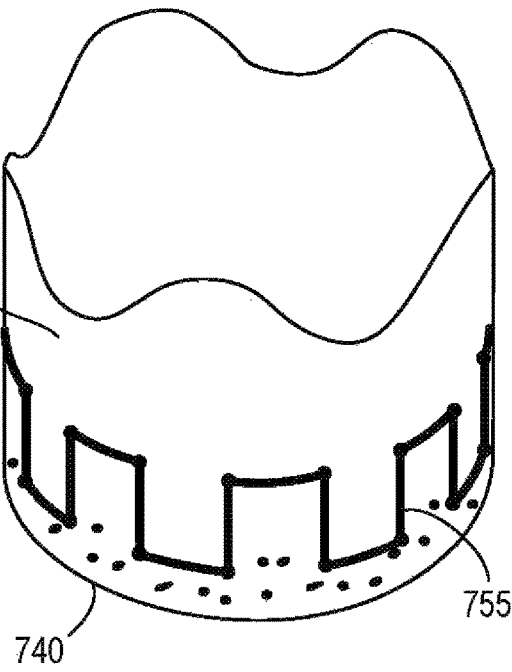
Figure 7D:
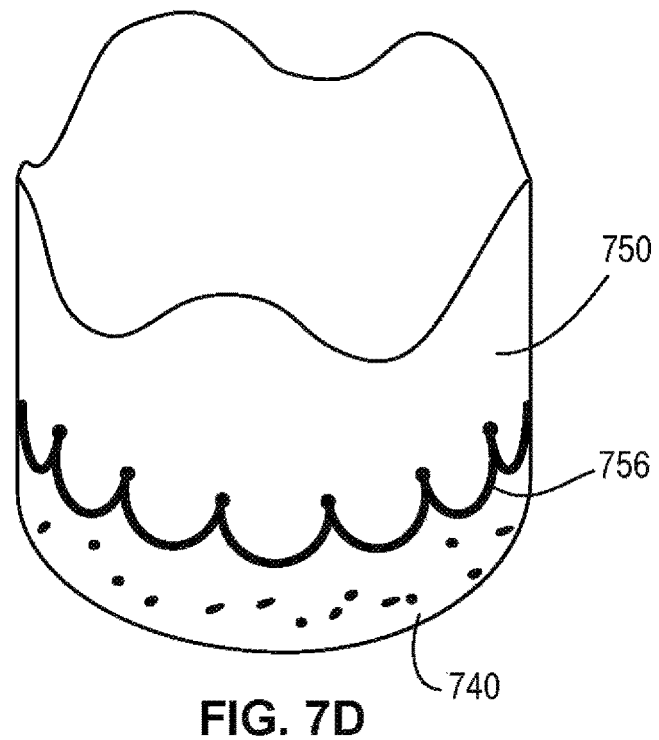

FIG. 7A shows a tubular seal 730 that includes an inflow end region 740 and an outflow end region 750. In some cases, at least a portion of tubular seal 730 can include a polymeric web. In some cases, the polymeric web can be a thin film, a porous layer, a mesh-like or net-like structure, or a porous network, e.g., a polymeric matrix. In some cases, for example, inflow end region 740 of tubular seal 130 can include a polymeric web. In some cases, inflow end region 740 can be a portion of a polymeric web retaining a fabric. In some cases, polymeric web can include an elastic material. In some cases, the polymeric web can include an elastomeric matrix.

In some cases, inflow end region 740 can be secured to bottom edges of a plurality of leaflets at an inflow end of a prosthetic heart valve provided herein, e.g., prosthetic heart valve 100, and have outflow end region 750 extend around an outer surface of an expandable member (e.g., a braided stent) to restrict blood flow around the leaflets. In some cases, a fabric can be embedded within the polymeric web such that the polymeric web forms a polymeric matrix around the fabric. In some cases, the polymeric web can include an elastic material. In some cases, an elastic polymeric web can conform to adjacent surfaces of a prosthetic heart valve provided herein to prove a resilient seal. The elastomeric polymer matrix can furthermore conform to the expandable member as the expandable member changed between a restricted configuration and an expanded configuration. In some cases, an elastic material can allow the tubular seal to return to its original length when the expandable member returns to the restricted configuration without tearing.

In some cases, at least a portion of the tubular seal 130, such as the polymeric web or matrix, can include one or more layers of an elastomeric polymer. In some cases, tubular seal 130 can include a polycarbonate, polyurethane, silicone, polytetrafluoroethylene (PTFE), or a combination thereof. Other suitable materials include, but are not limited to, natural and synthetic rubbers, including cis-1,4-polyisoprene rubber, styrene/butadiene copolymers, polybutadiene rubber, styrene/isoprene/butadiene rubber, butyl rubber, halobutyl rubber, polyurethane elastomers including elastomers based on both aromatic and aliphatic isocyanates, flexible polyolefins including flexible polyethylene and polypropylene homopolymers and copolymers, styrenic thermoplastic elastomers, polyamide elastomers, polyamide-ether elastomers, ester-ether or ester-ester elastomers, flexible ionomers, thermoplastic vulcanizates, flexible poly (vinyl chloride) homopolymers and copolymers, acrylic polymers, and a combination thereof. In some cases, tubular seal 130 can include an aliphatic polycarbonate-based thermoplastic urethane. In some cases, tubular seal 130 can include an elastomeric polymer having a hardness ranging from 3.07 MPa to 9.9 MPa, or a durometer ranging from 75 Shore A to 75 Shore D using ASTM standard D2240 in force on Jan. 1, 2014. In some cases, tubular seal 130 can include a polymeric material having the mechanical properties shown in Table I below. Notably, all of the listed ASTM standards refers to the standard in force on Jan. 1, 2014.

TABLE I

|  |  |  |  | ASTM Standard |
|---|---|---|---|---|
| Durometer Range Available | 75 Shore A-75 Shore D | | | D2240 |
| Specific Gravity | 1.10-1.14 | | | D792 |
| Melt Flow | 2-26 g/10 min(205° C./3.26 kg) | | | D1238 |
| MECHANICAL PROPERTY RANGES | | | | |
| Durometer | 75A-B20 | 55D | 75D | 75D |
| Ultimate Tensile Strength (psi) | 400-9000 | 5000-10000 | 3000-8000 | D638 |
| Tensile (psi) | | | | |
| @50% elongation | 350-650 | 1500-1800 | 3000-8000 | D638 |
| @100% elongation | 550-850 | 1800-2200 | 3000-8000 | D638 |
| @200% elongation | 600-1200 | 2800-4200 | | D638 |
| @300% elongation | 1200-2000 | 4200-10000 | | D630 |
| Ultimate Elongation (%) | 350-750 | 200-400 | 100-300 | D638 |

In some cases, referring back to FIGS. 1A and 1B, tubular seal 130 can include attachment structures, e.g., grommets 136, to improve the attachment of the tubular seal 130 to leaflets 200 and/or expandable member 110.

In some cases, tubular seal 730 can include a fabric retained by a polymeric web such that the fabric reinforces the polymeric web to allow the tubular seal to be secured to a prosthetic heart valve provided herein. Referring to FIG. 7A, for example, inflow end region 740 of tubular seal 730 can include a fabric embedded within an elastomeric material. Also shown in FIG. 7A, outflow end region 750 of tubular seal 730 can include a plurality of grommets 732. The fabric of inflow end region 740 can be a woven material. In some cases, the fabric can have warp threads and/or weft threads. In some cases, the fabric can be composed of fibers having an average thread diameter from about 0.5 microns to about 50 microns (or from about 0.00002 inches to about 0.002 inches), more preferably from about 20 micron to about 40 microns (or about 0.0008 inches to about 0.002 inches). More preferably, in some cases, the fabric is composed of fibers having a thread diameter of about 27 microns (or about 0.0011 inches).

In some cases, the fabric can include non-elastomeric fibers, or non-elastic fibers. Suitable non-elastomeric fiber materials include, but are not limited to, polyolefins, polyesters such as PES 38/31 manufactured by SaatiTech, and polyamides. More particularly, the polyolefins can include, for example, polyethylenes, polypropylenes, polybutenes, ethylene copolymers, propylene copolymers, butene copolymers, and combinations thereof. Because the fabric can include non-elastic fibers, inflow end region 740 and outflow end region 750 can have different overall elastic properties.

As shown in FIG. 7A, the fabric of a tubular seal has a non-linear edge defining an interface 753 between inflow end region 740 and the outflow end region 750. In some cases, interface 753 between the inflow end region 740 and the outflow end region 750 can be non-linear due to a non-linear edge of the fabric within inflow end region 740. As shown in FIG. 7A, the non-linear edge can be sinusoidal 753. In some cases, as shown in FIGS. 7C-7F, the non-linear edge can be a zigzagged edge 754, a stepped edge 755, or a scalloped edge 756,772, 782.

Figure 7E:
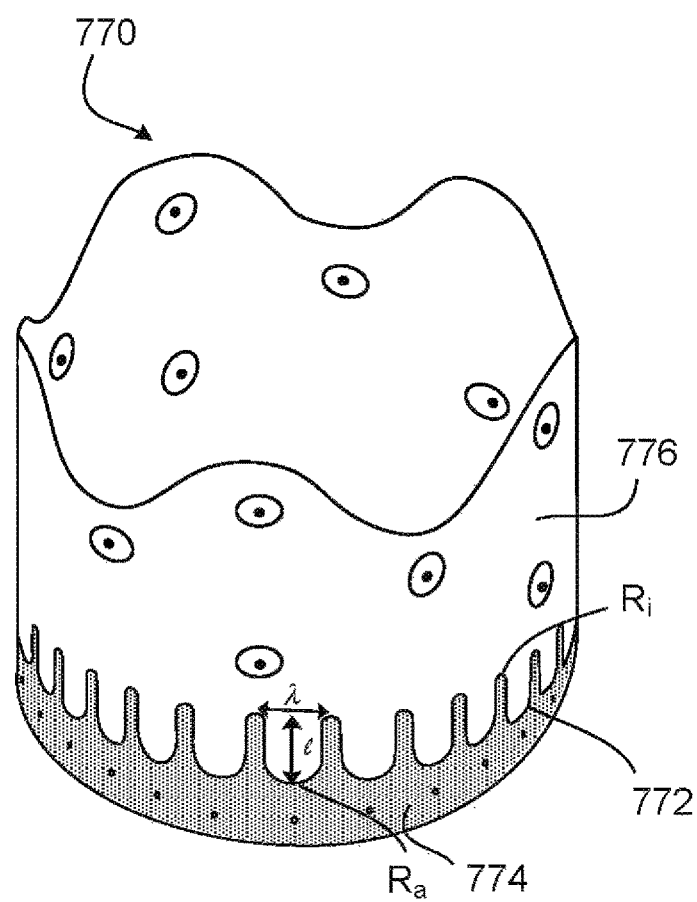
Figure 7F:
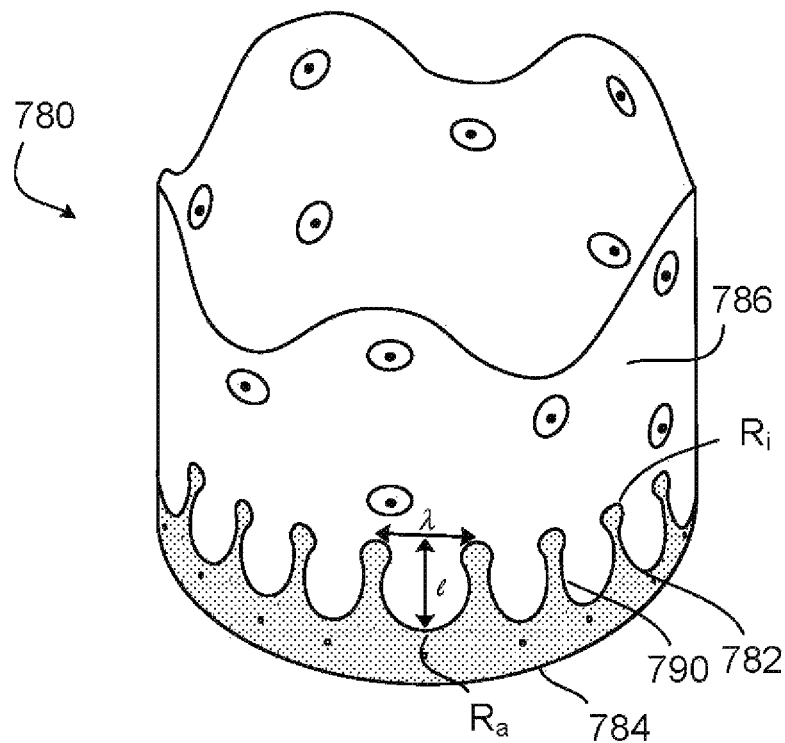

FIGS. 7E and 7F provide alternative embodiments of tubular seals 770, 780 having scalloped, non-linear edges. As shown, the scalloped, non-linear edges define non-linear circumferential interfaces 772, 782 between an inflow end region 774, 784 and an outflow end region 776, 786. Interfaces 772, 782, as shown in FIGS. 7E and 7F, have a scalloped shape defined by a major radius $R_a$, a minor radius $R_i$, a wavelength ($\lambda$) and a transition zone length (l). In some cases, major radius $R_a$ can be the radius proximate the inflow end region and minor radius $R_i$ can be the radius proximate the outflow end region. In some cases, major radius $R_a$ can be the radius proximate the outflow end region and minor radius $R_i$ can be the radius proximate the inflow end region. As shown in FIGS. 7E and 7F, major radius $R_a$ is larger than the minor $R_i$. In some cases, major and minor radii $R_a$, $R_i$ are equal and form a sinusoidal-shaped interface. In some cases, the ratio between major radius $R_a$ and minor radius $R_i$ can range from 1:1 to 2:1, 2:1 to 3:1, from 3:1 to 4:1, or from 4:1 to 5:1. In some cases, a necked region 790 (see FIG. 7F) can be formed between minor radius $R_i$ and major radius $R_a$. In some cases, minor radius $R_i$ can form bulbous ends, as shown in FIG. 7F, to increase the interface length and improve durability of tubular seal 780 at or near interface 782. The interfaces described herein provide the benefit of preventing or minimizing tear propagation in the tubular seal while providing sufficient bond strength to maintain the bond between the inflow and outflow end regions of the tubular seal. In some cases, the interfaces described herein can prevent or minimize a tear from propagating further at the interface region by redirecting the tear or by providing a barrier to the tear.

In some cases, the major radius $R_a$ and/or the minor radius $R_i$ can range from about 1.3 millimeters to about 2.54 millimeters (or about 0.050 inches to about 0.100 inches), from about 1.8 millimeters to about 2.0 millimeters (or about 0.070 inches to about 0.080 inches), from about 2.0 millimeters to about 2.54 millimeters (or about 0.080 inches to about 0.100 inches), or from about 2.3 millimeters to about 2.4 millimeters (or about 0.090 to about 0.095 inches). In some cases, the major radius $R_a$ and/or the minor radius $R_i$ can range from about 0.51 millimeters to about 0.76 millimeters (or about 0.020 inches to about 0.030 inches), from about 0.76 millimeters to about 1.0 millimeters (or about 0.030 inches to about 0.040 inches), from about 1.0 millimeters to about 1.3 millimeters (or about 0.040 inches to about 0.050 inches), from about 0.51 millimeters to about 1.0 millimeters (about 0.020 inches to about 0.040 inches), or from about 0.51 millimeters to about 1.3 millimeters (or about 0.020 inches to about 0.050 inches). In some cases, the wavelength (λ) of the scalloped-shaped interface, or the length of one repeating scallop shape, can range from about 2.5 millimeters to about 1.0 millimeters (or about 0.10 inches to about 0.40 inches), from about 3.8 millimeters to about 5.1 millimeters (or about 0.15 inches to about 0.20 inches), or from about 5.1 millimeters to about 6.35 millimeters (or about 0.20 inches to about 0.25 inches). There can be various suitable lengths of the transition zone length described herein. The transition zone length can be measured as a distance between the crest of the minor radius $R_i$ and the trough of the major radius $R_a$. In some cases, the transition zone length can range from about 2.8 millimeters to about 3.0 millimeters (or about 0.110 inches to about 0.120 inches), from about 3.0 millimeters to about 3.3 millimeters (or about 0.120 inches to about 0.130 inches), from about 3.3 millimeters to about 3.6 millimeters (or about 0.130 inches to about 0.140 inches), from about 3.6 millimeters to about 3.8 millimeters (or about 0.140 inches to about 0.150 inches), from about 3.8 millimeters to about 4.1 millimeters (or about 0.150 inches to about 0.160 inches), or from about 2.8 millimeters to about 4.1 millimeters (or about 0.110 inches to about 0.160 inches).

Referring back to FIG. 7A, in some cases, inflow end region 740 can be thicker than outflow end region 750 because of the presence of a fabric within inflow end region 740. In some cases, inflow end region 740 can have a thickness of about 70 microns (0.0028 inches). In some cases, outflow end region 750 can have a thickness of about 50 microns (about 0.0020 inches). Other suitable thicknesses for inflow end region 740 include thicknesses ranging from about 50 microns to about 90 microns (about 0.0020 inches to about 0.0035 inches), or more preferably, from about 60 microns to about 80 microns (about 0.0025 inches to about 0.0031 inches). Suitable thicknesses for outflow end region 750 include thicknesses ranging from about 30 microns to about 70 microns (about 0.0011 inches to about 0.0028 inches), or more preferably, from about 40 microns to about 60 microns (about 0.0016 inches to about 0.0023 inches). In some cases, suitable thickness ratios of inflow end region 740 relative to outflow end region 750 can range from 1:1 to 1.2:1, from 1.2:1 to 1.4:1, from 1.4:1 to 1.5:1, and from 1.5:1 to 2:1. A non-linear edge can providing a non-linear interface, e.g., interface 753, between inflow end region 740 and outflow end region 750. A prosthetic heart valve that has non-linear interface 753 may have an increased overall diameter that tapers more gradually than a prosthetic heart valve that has a linear interface. The non-linear edge of the fabric can gradually transition the change in elastic properties between the outflow end region 750 and inflow end region 740, mitigating the formation of stress concentrators along an interface that can cause tearing in the tubular member. Additionally, the non-linear shape of interface 753 can minimize or prevent the propagation of tears.

Still referring to FIG. 7A, in some cases, the fabric can be arranged in inflow end region 740 to allow for the fabric within inflow end region 740 to stretch in axial and/or radial directions to allow tubular seal 730 to stretch along with an expandable member during implantation. When the fabric does not allow a tubular seal to adequately stretch, the seal can cause non-uniform crimping during manufacturing or damage the expandable member during device deployment. In some cases, a woven fabric can be arranged to have the warp and the waft extend in directions oblique to the axis of tubular seal 730. This can allow the fabric to flex in radial and/or axial directions relative to the axis of tubular seal 730, but limit the fabric from stretching in a direction oblique to the axis. In some cases, both the warp and the waft can extend at an angle between 30 degrees and 60 degrees with the axis of tubular seal 730. In some cases, both the warp and the waft can extend at an angle between 5 degrees and 70 degrees with the axis of tubular seal 730. In some cases, the warp and waft can be arranged within the tubular member 730 to form an angle of about 45 degrees with the axis of tubular seal 730. In some cases, the fabric can be a knit fabric arranged to allow for a predetermined amount of stretch in the axial and/or radial directions. Limiting the fabric within inflow end region 740 from stretching in a direction oblique to the axis can prevent the fabric from bunching and minimize non-uniform crimping during manufacturing.

Additional exemplary tubular seals including a fabric and grommets are described in U.S. Patent Application No. 2013/0090729, which is hereby incorporated by reference in its entirety. For example, U.S. Pat. No. 8,778,020 describes a seal that includes a multilayer, cylindrical seal body having projections alternating with recesses along the proximal edge of the seal body with proximal reinforcing grommets and a distal reinforcing band, which may be formed from a woven or nonwoven fabric and either incorporated within the interior of the multilayer seal body or adhered to the surface thereof.

In some cases, tubular seals described in U.S. Patent Application No. 2013/0090729 can be modified to include a fabric arrangement that allows a seal to stretch in axial and/or radial directions. In some cases, elastomeric materials provided herein can be incorporated into the tubular seals disclosed in U.S. Patent Application No. 2013/0090729. In some cases, the tubular seals described in U.S. Patent Application No. 2013/0090729 can be modified to include the non-linear interface 753 provided herein.

Still referring to FIG. 7A, tubular seal 730 can be created by producing one or more layers of elastomeric polymer, applying the fabric and grommets 732 to the one or more layers of elastomeric polymer, and overcoating the fabric and grommets 732 with one or more additional layers of elastomeric material. In some cases, different layers can have different elastomeric properties. In some cases, tubular seals (e.g., 130, 730, or 760) can include a radially innermost layer including at least one elastomeric polymer, e.g., a polycarbonate and a polyurethane; a radially outermost layer including at least one elastomeric polymer, e.g., a polycarbonate and a polyurethane; and at least one inner layer disposed between the radially outermost layer and a radially innermost layer. In some cases, the modulus of elasticity of the innermost layer is less than the modulus of elasticity of the radially innermost outer layer and the modulus of elasticity of the radially outermost outer layer. In some cases, the elongation to break of the inner layer is greater than the elongation to break of the radially innermost outer layer and the elongation to break of the radially outermost outer layer. Although the radially innermost outer layer and the radially outermost outer layer have been depicted as including the same material, it will be appreciated that they may be compositionally the same or different.

The multilayer tubular seals provided herein (e.g., 130, 730, 760) may be formed in a variety of ways. In some cases, multilayer tubular seals provided herein may be formed by successive applications of a polymer solution to an appropriately shaped mandrel, such as that illustrated in FIG. 6.

Following a careful cleaning of the mandrel 600, the mandrel may be mounted to an appropriate holding fixture in a spray booth. A first coating composition including a carrier and at least one polymer may be applied to the mandrel 600 and subsequently dried to form a first coated mandrel. In some cases, the first coating composition includes one or more elastomeric polymers, e.g, polycarbonate and/or a polyurethane, and a volatile carrier. The coating composition may be applied as a single layer or multiple layers to achieve the desired dried coating thickness. The grommets 732 (FIG. 7A) and the fabric may be positioned on the first coated mandrel by inserting locating pins 620 in apertures 610 in the tapered mandrel 600 of FIG. 6 that align with corresponding perforations 30 provided in the grommets 32, 34, 36 and the fabric 40. In FIG. 6, only one pin 620 has been illustrated for clarity. In some instances, it may be desirable to secure the plurality of grommets 732 and the fabric to the mandrel or to an underlying coating layer by applying a drop of a first coating composition, or other adhesive composition, to each item to ensure that it remains properly positioned during subsequent processing. The fabric can be cut to a suitable shape having a non-linear edge using any suitable method. In some cases, the fabric can be die cut. In some cases, the fabric can be cut with a blade. In some cases, the fabric can be cut using a femtosecond laser. In some cases, a femtosecond laser cut fabric mitigates the chances of forming stress concentrators along the edge of the fabric.

A second coating composition including a carrier and at least one polymer may be applied to the first coated mandrel, the fabric, and the plurality of grommets. In some cases, the second coating composition includes one or more elastomeric polymers, e.g, polycarbonate and/or a polyurethane, and a volatile carrier. The carrier of the second coating composition may be removed, thereby forming a second coated mandrel. The second coating composition may be applied as a single layer or as multiple layers to achieve the desired dried coating thickness. In some cases, the second coating composition may be different from the first coating composition. In some cases, the second coating composition may be composed of the same material as the first coating composition.

In some cases, a third coating composition including a carrier and at least one polymer may be applied to the second coated mandrel. In some cases, the third coating composition includes one or more elastomeric polymers, e.g, polycarbonate and/or a polyurethane, and a volatile carrier. The carrier of the third coating composition may be removed thereby forming a tubular seal precursor. The third coating composition may be applied as a single layer or as multiple layers to achieve the desired dried coating thickness. In some cases, the third coating composition may be different from the first coating composition. In some cases, the third coating composition may be the same as the first coating composition. In some cases, the third coating composition may be different from the second coating composition. In some cases, the third coating composition may be the same as the second coating composition. Following removal of the carrier from the third coating composition, the tubular seal precursor may be inspected to ensure that it is fully formed and meets dimensional specifications, such as a thickness specification. In some cases, a suitable thickness for the tubular seal precursor can range from about 30 microns to about 75 microns (about 0.001 inches to about 0.0030 inches) or from about 50 microns to about 120 microns (about 0.002 inches to about 0.0047 inches). Other suitable thicknesses for the tubular seal precursor include a range from about 20 microns to about 40 microns (about 0.0008 inches to about 0.002 inches), about 30 microns to about 50 microns (about 0.001 inches to about 0.002 inches), about 50 microns to about 75 microns (about 0.002 inches to about 0.0029 inches), about 50 microns to about 100 microns (about 0.002 inches to about 0.004 inches), about 100 microns to about 120 microns (about 0.004 inches to about 0.0047 inches), about 100 microns to about 150 microns (about 0.004 inches to about 0.0059 inches), about 150 microns to about 200 microns (about 0.0059 inches to about 0.0079 inches), as well as any thickness value within any of the listed ranges.

In some cases, the tubular seal precursor may be inspected to ensure that it meets certain functional specifications, e.g., tensile and frictional specifications. The tubular seal precursor may then be trimmed by laser cutting, or blade cutting, to conform to dimensional specifications and removed from the tapered seal-forming mandrel as a formed tubular seal. In some cases, at least some preformed apertures for suturing tubular seal to expandable member 110 and/or leaflets 200 (see FIGS. 1A and 1B) can be performed by laser cutting. In some cases, at least some of the grommets may be formed by a laser cutting operation performed on a tubular seal precursor. In some cases, grommets 732 of FIG. 7A may be added to the multilayer, generally cylindrical seal, in a step not illustrated, as a proximal band. Subsequent laser cutting of the tubular seal precursor would then simultaneously form grommets 732 by removing the portions of the proximal band located between the projections.

In some cases, coating compositions may be selected to provide a relatively stiff dried polymer such as a dried polymer having a Shore D hardness of about 55, or a hardness of about 6.21 Megapascals (MPa). In some cases, coating compositions may be selected to provide a relatively elastomeric dried polymer such as a dried polymer having a Shore A hardness of about 80, or a hardness of about 3.45 MPa. In some cases, the first and third dried polymer layers may have a Shore D hardness of 55, or a hardness of 6.21 MPa, and the second layer may have a Shore A hardness of 80, or a hardness of 3.45 MPa.

Although in some cases described above, three polymer layers were employed, it will be appreciated that a greater or lesser number of layers may be employed and that each of the three or more layers may include two or more sublayers. In some cases, the plurality of grommets and the fabric can be positioned between the first and second coating layers. In some cases, the plurality of grommets and the fabric can be positioned elsewhere within the tubular seal, e.g., within a layer, or on the radially innermost or radially outermost surface of the tubular seal.

Figure 7G:
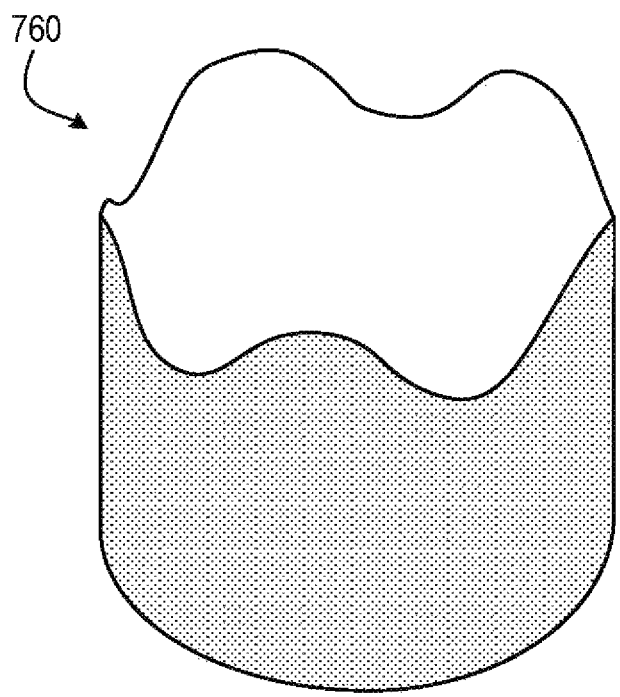

As shown in FIG. 7G, a tubular seal 760 can include a woven or non-woven fabric embedded throughout a polymer or metal matrix structure. In some cases, at least one leaflet of the heart valve can be secured to the tubular seal in a portion of the tubular seal including the woven or non-woven fabric to minimize blood leakage between the tubular seal and the leaflets.

Figure 8A:
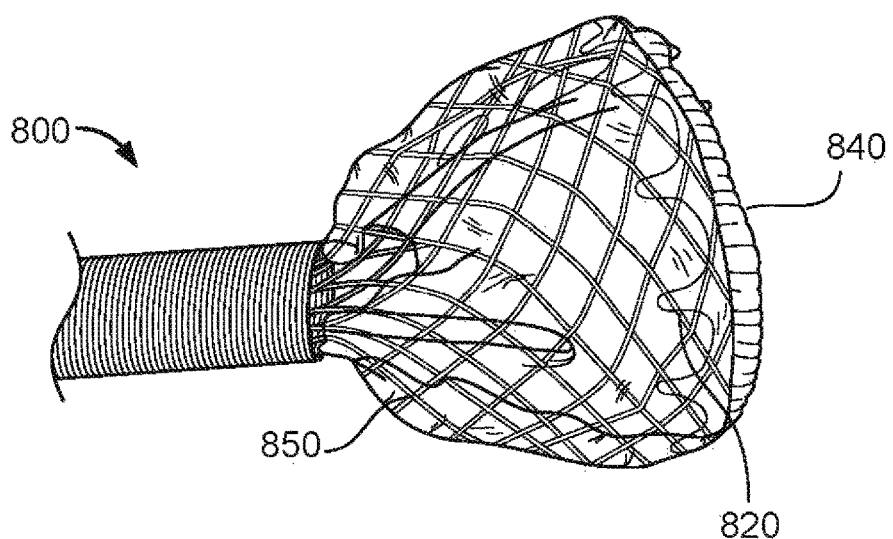
FIGS. 8A-8C illustrate an exemplary tubular seal having a scalloped, non-linear edge in a prosthetic heart valve provided herein.
Figure 8B:
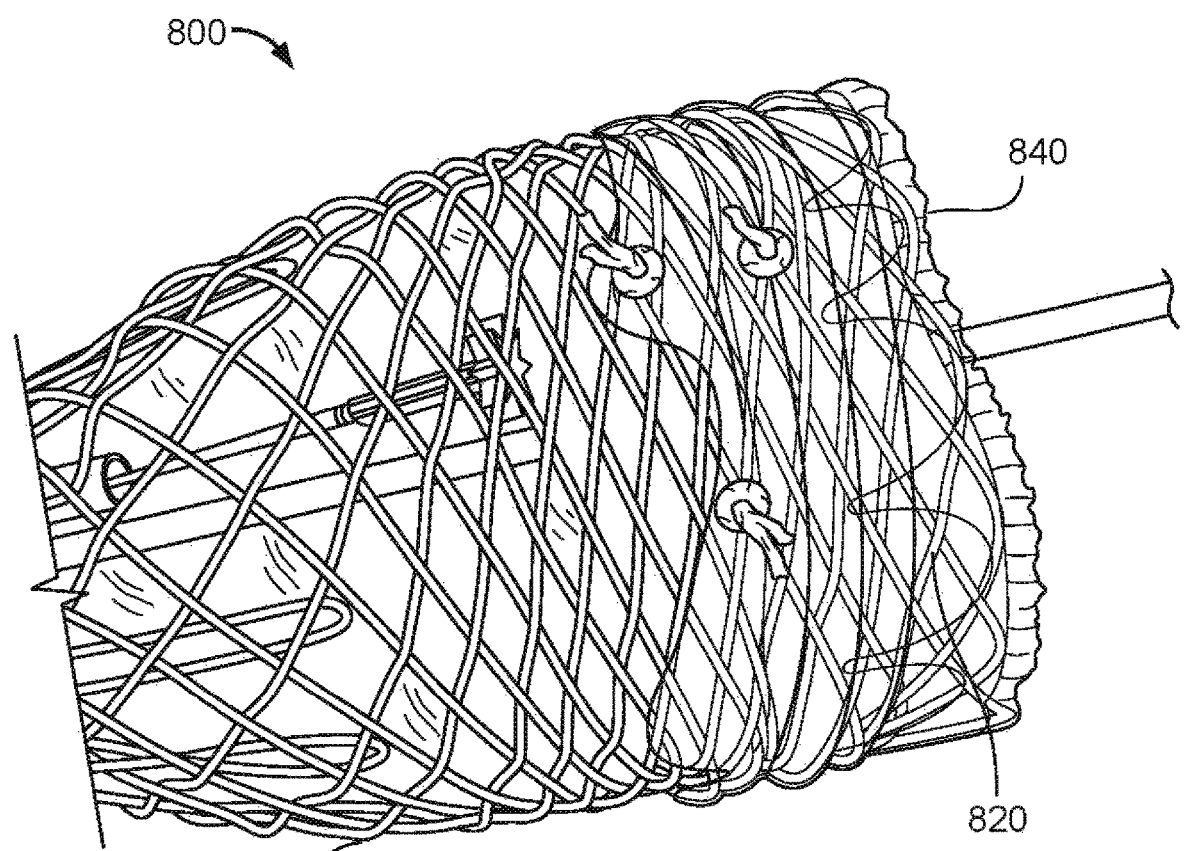
Figure 8C:
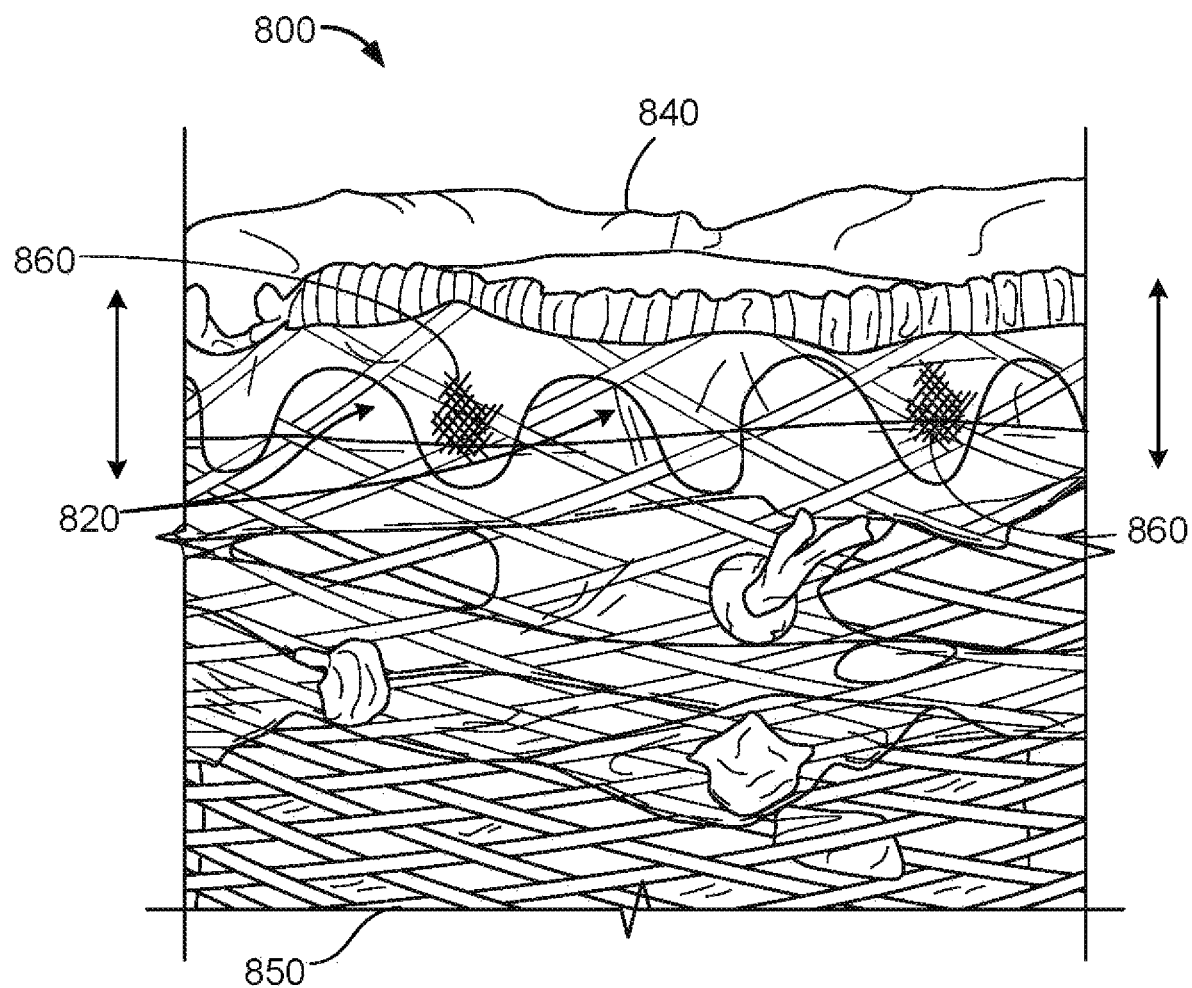

FIGS. 8A-8C are illustrations of an exemplary tubular seal 800 secured to an exemplary prosthetic heart valve provided herein. Tubular seal 800, as shown in FIGS. 8A-8C, includes a non-linear edge interface 820 between an inflow end region 840 and an outflow end region 750. FIG. 8A shows tubular seal 800 advancing from a distal end of a deployment device provided herein and expanding radially. FIG. 8B provides an illustration of tubular seal 800 in a further radially expanded and deployed state. FIG. 8C provides a close up illustration of non-linear interface 820 of tubular seal 800.

Referring to FIGS. 8B and 8C, tubular seal 800 includes a fabric in inflow end region 840 that has a non-linear edge defining a non-linear circumferential interface 820 between inflow end region 840 and outflow end region 850. As shown in FIGS. 8A-8C, the non-linear edge of the fabric forms a scalloped-shaped interface 820. In some cases, the non-linear edge can form a sinusoidal, scalloped, or zigzagged shaped interface. The non-linear interface between inflow end region 840 and outflow end region 850 can disperse stress that forms along the interface during stretching of the tubular seal, limit or redirect tear propagation in outflow end region 850 back towards inflow end region 840, and provide a transition zone where the overall outer diameter of the tubular member transitions between a thinner outflow end region thickness to a thicker inflow end region thickness. Variations in thickness between inflow end region 840 and outflow end region 850 can be due to the presence of the fabric within inflow end region 840. In some cases, a tubular seal having a non-linear interface can exhibit a different tensile failure mode than a tubular seal with a linear interface, because the tear propagation has been limited or redirected at interface 820. Advantages of having non-linear interface 820 thus includes increasing the durability of tubular seal 800 at interface 820.

In some cases, prosthetic heart valves provided herein include a tubular seal including a woven fabric within an elastomeric matrix where the woven fabric has a non-linear edge within the elastomeric matrix around the circumference of the tubular seal. In some cases, the matrix structure can be made of elastomeric material. In some cases, tubular seal 800 can be made of the fabric alone.

Still referring to FIGS. 8A-8C, non-elastic fibers 860 can be part of a knit fabric used in tubular seals provided herein. In some cases, the fabric is a woven or nonwoven fabric having non-elastic fibers 860 arranged to allow the seal radially expand. The fabric can, for example, include non-elastic fiber 860 arranged to allow a portion of tubular seal 800 to stretch in axial and/or radial directions relative to the axis of the tubular seal 800. In some cases, the woven fabric having non-elastic fiber 860 can be positioned along a front edge of a tubular seal positioned to be secured to an expandable member. In some cases, the non-elastic fiber 860 can be arranged at an of between 5 degrees and 70 degrees relative to a central axis of the tubular seal such that the non-elastic fiber 860 allow for a limited stretching of the tubular seal in an axial direction and/or a radial direction. For example, the non-elastic fiber 860 can be part of a woven fabric having fiber in a warp direction and fibers in a waft direction each oriented at an angle of between 5 degrees and 70 degrees relative to a central axis of the tubular seal. Although the non-elastic fiber 860 do not individually stretch, a woven structure can be stretched in directions non-parallel with the orientation of the fiber 860. In some cases, the non-elastic fiber 860 can be arranged within the tubular member 760 to form an angle of about 45 degrees with the axis of the tubular seal. In some cases, the fabric can be a knit fabric arranged to allow for a predetermined amount of stretch in the axial and/or radial directions.

In some cases, fibers 860 of the fabric can allow for the expandable member to be secured to the leaflets and/or to the expandable member. For example, stitches or sutures can extend around the non-elastic fiber 860 within the matrix to ensure that the stitches or sutures do not cause the tubular seal to tear. Tears in the tubular seal can result in leakage of blood past a prosthetic heart valve, which can result in heart failure.

In some cases, the non-elastic fiber 860 within the tubular seal can be dispersed throughout a matrix structure, e.g., an elastomeric polymer matrix. In some cases, a fabric of the non-elastic fiber 860 can be throughout the tubular seal. The fabric within the matrix, e.g., an elastomeric polymer matrix, can be arranged to allow for a limited amount of expansion of the tubular seal in a radial direction and/or an axial direction. As discussed below in further detail, non-elastic fiber 860 dispersed throughout the tubular seal can simplify the production of the tubular seal, allow for sutures to be used to attach any section of the tubular seal to one or more other portions of a prosthetic heart valve provided herein, and provide a substantially uniform thickness. A tubular seal having a uniform thickness can facilitate loading of a prosthetic heart valve provided herein into a delivery sheath because non-uniform sections of a seal can catch on a delivery sheath and potentially tear the tubular seal.

In some cases, a tubular seal provided herein can include an inflow end region and an outflow end region with the inflow end region including a fabric of non-elastic fiber 860. The inflow end region can be secured to the bottom edges of leaflets and/or an inflow end of the expandable member by stitches and/or sutures. In some cases, an outflow end region can include grommets for attachment to an outer surface of the expandable member. In some cases, the fabric can be arranged to allow for the inflow end region to be expanded in a radial and/or axial direction, which can mitigate the transition in elasticity at the interface between an inflow end region and the outflow end region. An abrupt transition in elasticity between the inflow end region and the outflow end region can result in a stress concentrator along the interface, which can result in a tear along the interface. By having a fabric oriented in the inflow end region to allow axial and/or radial expansion of the inflow end region can disperse stresses formed along the interface during stretching of the tubular seal.

In some cases, the fabric can be made of polymeric materials that include, but are not limited to, polyesters, polyolefins such as polyethylene and polypropylene, polyamides, nylons, and combinations thereof. In some cases, the fabric can have a thickness ranging from about 40 to about 80 microns (about 0.002 inches to about 0.003 inches). In some cases, the fabric can be woven such that spacings between individual fiber 860 create openings in the fabric that together constitutes from about 20% to about 40% of a fabric surface.

A tubular seal having a fabric embedded throughout the elastomeric material can simplify the manufacturing process. For example, instead of requiring the use of the mandrel 600 to build up layers of elastomeric polymer and position a fabric in select portions of the tubular seal, tubular seal 800 can be created by coating a continuous tube of fabric including non-elastic fiber 860 with an elastomeric polymer and cutting the tube into individual tubular seals or portions of tubular seals. In some cases, portions of the tubular seal having fabric can be created on a separate mandrel and later bonded to portions of the tubular seal that do not have fabric. In some cases, a tube of fabric can be stretched in an axial direction during the coating of the fabric with the elastomeric polymer to enable the tubular seal to have more stretch in a radial direction than an axial direction.

A number of embodiments of the invention have been described. Nevertheless, it will be understood that various modifications may be made without departing from the spirit and scope of the invention. Accordingly, other embodiments are within the scope of the following claims.

What is claimed is:

1. A tubular seal for a prosthetic heart valve comprising: an elastomeric polymer matrix and a woven fabric embedded within the polymer matrix, the woven fabric comprising a plurality of non-elastic fibers retained within an inflow end region of the elastomeric polymer matrix, wherein the woven fabric comprising a non-linear edge embedded within the elastomeric polymer matrix.

2. The tubular seal of claim 1, wherein the non-linear edge of the woven fabric has a sinusoidal or scalloped shape defining an interface between the inflow end region and an outflow end region of the elastomeric polymer matrix.

3. The tubular seal of claim 2, wherein the interface has a major radius $R_a$ that ranges from about 0.050 inches to about 0.100 inches.

4. The tubular seal of claim 2, wherein interface has a minor radius $R_a$ that ranges from about from about 0.020 inches to about 0.040 inches.

5. The tubular seal of claim 2, wherein the interface has a transition zone length that ranges from about 0.110 inches to about 0.160 inches.

6. The tubular seal of claim 1, wherein the non-elastic fibers comprise a polyester.

7. The tubular seal of claim 1, wherein the elastomeric polymer matrix comprises a polymer selected from polycarbonates, polyurethane, silicones, and combinations thereof.

8. The tubular seal of claim 1, wherein the inflow end region comprises a first substantially uniform thickness and an outflow end region of the elastomeric polymeric matrix comprises a median thickness that is less than the first substantially uniform thickness.

9. The tubular seal of claim 1, wherein a thickness for the inflow end region ranges from about 0.0016 inches to about 0.0023 inches, or from about 40 microns to about 60 microns.

* * * * *